(12) United States Patent
Stevens

(10) Patent No.: US 8,011,026 B2
(45) Date of Patent: Sep. 6, 2011

(54) FACE MASK AND GOGGLE SYSTEM

(75) Inventor: Simon Benjamin Stevens, Sewell, NJ (US)

(73) Assignee: Kee Action Sports I LLC, Sewell, NJ (US)

(*) Notice: Subject to any disclaimer, the term of this patent is extended or adjusted under 35 U.S.C. 154(b) by 1135 days.

(21) Appl. No.: 11/437,170

(22) Filed: May 19, 2006

(65) Prior Publication Data

US 2007/0050896 A1    Mar. 8, 2007

Related U.S. Application Data

(60) Provisional application No. 60/682,566, filed on May 19, 2005.

(51) Int. Cl.
*A61F 9/02* (2006.01)

(52) U.S. Cl. .............................. 2/427; 2/429

(58) Field of Classification Search .............. 2/410, 242, 2/425, 15, 426, 427, 429, 10, 428, 430, 431, 2/9

See application file for complete search history.

(56) References Cited

U.S. PATENT DOCUMENTS

| | | |
|---|---|---|
| 3,259,908 A | 7/1966 | Simpson et al. |
| 3,783,452 A | 1/1974 | Benson et al. |
| 3,789,428 A | 2/1974 | Martin |
| 4,150,443 A | 4/1979 | McNeilly |
| 4,317,240 A | 3/1982 | Angerman et al. |
| D277,520 S | 2/1985 | Gregory |
| D284,327 S | 6/1986 | Gregory et al. |
| D285,381 S | 9/1986 | Dawson et al. |
| 4,617,686 A | 10/1986 | Nahas |
| 5,018,223 A | 5/1991 | Dawson et al. |
| 5,148,550 A * | 9/1992 | Hodgkinson et al. ............ 2/424 |
| 5,365,615 A | 11/1994 | Piszkin |
| 5,642,530 A | 7/1997 | Parks |
| 5,657,493 A | 8/1997 | Ferrero et al. |
| 5,666,671 A | 9/1997 | Daneshvar |

(Continued)

FOREIGN PATENT DOCUMENTS

JP    10-71167    3/1998

OTHER PUBLICATIONS

Vforce, Mask Care and Use Instructions.

(Continued)

*Primary Examiner* — Khoa D Huynh
*Assistant Examiner* — Sally C Cline
(74) *Attorney, Agent, or Firm* — Volpe and Koenig, P.C.

(57) ABSTRACT

A protective face mask system according to the present invention comprises a flexible mask body including an opening for receiving a lens, nose portion, a central portion positioned to the rear of and extending at least partially above the nose portion, a central receiving slot located between the nose portion and the central portion, right and left temple portions, each temple portion having a shaped receiving opening therethrough, left and right cheek portions, and at least one groove located adjacent one of the left and right cheek portions. A lens is provided sized to be received upon and cover the lens opening. The lens includes right and left temple portions including openings therein positioned to correspond to and align with the openings of the mask body when the lens is positioned for attachment to the mask body. The lens including at least a portion that snappingly engages the groove when a portion of the lens is inserted into the slot.

7 Claims, 21 Drawing Sheets

U.S. PATENT DOCUMENTS

| | | | |
|---|---|---|---|
| 5,689,834 A | 11/1997 | Wilson | |
| 5,809,580 A | 9/1998 | Arnette | |
| D407,858 S | 4/1999 | Cyr et al. | |
| 5,911,308 A | 6/1999 | Chafitz et al. | |
| 6,094,751 A | 8/2000 | Parks | |
| 6,138,285 A | 10/2000 | Robrahn et al. | |
| 6,149,268 A | 11/2000 | Hall et al. | |
| 6,321,391 B1 | 11/2001 | Basso | |
| 6,349,419 B1 * | 2/2002 | Chiang | 2/428 |
| 6,349,420 B1 * | 2/2002 | Chiang | 2/428 |
| 6,363,528 B1 | 4/2002 | Cyr | |
| 6,381,749 B1 * | 5/2002 | Cyr | 2/9 |
| D459,837 S | 7/2002 | Dupuis | |
| 6,425,143 B1 | 7/2002 | Benedict et al. | |
| 6,560,788 B1 | 5/2003 | Beltrani | |
| 6,644,308 B2 | 11/2003 | Kalhok et al. | |
| D487,534 S | 3/2004 | Broersma | |
| D497,039 S | 10/2004 | DeHaan et al. | |
| D497,223 S | 10/2004 | Kalhok | |
| 6,874,169 B2 | 4/2005 | Broersma | |
| 6,886,183 B2 | 5/2005 | DeHaan et al. | |
| 6,896,366 B2 | 5/2005 | Rice et al. | |
| 6,948,813 B2 * | 9/2005 | Parks | 351/158 |
| 6,957,447 B1 | 10/2005 | Broersma | |
| 7,003,802 B2 * | 2/2006 | Broersma | 2/9 |
| D518,605 S | 4/2006 | Chen | |
| D522,697 S | 6/2006 | Chen | |
| D526,094 S | 8/2006 | Chen | |
| D527,847 S | 9/2006 | Broersma | |
| D529,234 S | 9/2006 | Broersma | |
| D529,662 S | 10/2006 | Broersma | |
| D536,833 S | 2/2007 | Broersma | |
| D570,550 S | 6/2008 | Broersma | |
| D570,551 S | 6/2008 | Broersma | |
| D570,552 S | 6/2008 | Broersma | |
| D571,050 S | 6/2008 | Broersma et al. | |
| D586,050 S * | 2/2009 | Chen | D29/110 |
| D601,308 S | 9/2009 | Broersma | |
| RE41,834 E | 10/2010 | Parks | |
| 2003/0167558 A1 | 9/2003 | Broersma | |
| 2003/0223032 A1 | 12/2003 | Gagnon et al. | |
| 2004/0049825 A1 | 3/2004 | DeHaan et al. | |
| 2004/0103469 A1 | 6/2004 | Hussey | |
| 2004/0111779 A1 | 6/2004 | Gagnon et al. | |
| 2004/0139532 A1 | 7/2004 | Parks | |
| 2005/0150028 A1 | 7/2005 | Broersma | |
| 2005/0204446 A1 | 9/2005 | Wright | |
| 2005/0278833 A1 * | 12/2005 | Pierce | 2/424 |
| 2006/0090234 A1 | 5/2006 | Cyr | |
| 2006/0117467 A1 * | 6/2006 | Choi et al. | 2/424 |
| 2006/0272067 A1 | 12/2006 | Gagnon et al. | |
| 2007/0186324 A1 | 8/2007 | Sheldon et al. | |
| 2007/0192946 A1 * | 8/2007 | Wright | 2/424 |

OTHER PUBLICATIONS

Vforce, Mask Manual.
Goggle Lens Manual
HeadShield Manual_1.
HeadShield Manual_2.
FX-10 Manual_1.
FX-10 Manual_2.
Universal Sportz-Comm Manual_1.
Universal Sportz-Comm Manual_2.
Helmet Manual.
Goggle Lens Manual—Mexico.
Goggle Manua I—China.
HeadShield Manual.
QLS Goggle Lens OM.
QLS Goggle OM V2.
Generic Goggle OM.
Vforce Use Care Pamphlet.
www.vforcepaintball.com_docs_manual.
PROtector_manual_eng.
Use_care.
VL_2008Catalog.

* cited by examiner

FACE MASK AND GOGGLE SYSTEM

CROSS REFERENCE TO RELATED APPLICATION

This application claims priority from U.S. Provisional Patent Application No. 60/682,566, the entire contents of which is incorporated by reference as if fully set forth herein.

FIELD OF INVENTION

The present invention generally relates to the field of protective gear, and more specifically, to the field of protective face mask and goggle systems for sports.

BACKGROUND

Paintball is a popular sporting game. It is played on a field including obstacles. Generally, teams of players each have a flag located at the team's home base. The object of the game is to "capture" the opposing team's flag before they capture yours. Each player is armed with a paintball marker for firing projectiles. Most paintball markers are compressed gas guns that shoot projectiles, otherwise known as paintballs. Paintballs are generally spherical gelatin capsules filled with paint, normally a non-toxic marking dye. If a player is hit with and marked by a paintball fired by a player on the opposing team that player is eliminated from the game.

All players in the sport of paintball, and other action or recreation combat sports such as airsoft, must wear protective equipment. One piece of protective equipment that must be worn is a face mask, which may incorporate goggles to protect the eyes, or may otherwise have protective lenses.

Known face mask and goggle systems suffer from various inadequacies. When a projectile, such as a paintball, impacts known face masks or goggles near the nose portion of the face mask or goggles, the lens portion of the mask or goggle tends to separate from the body of the mask or goggle. creating an opening. Projectile material can pass through the opening, partially or wholly defeating the purpose of the mask or goggle.

In addition, the lens of a face mask or goggle should preferably be easily replaceable. Current face masks and goggles have complicated arrangements for attaching lenses to the body of the face mask or goggle. These known face masks and goggles make it is difficult to easily and efficiently replace and/or clean the lenses when necessary.

Furthermore, current face mask and goggle systems do not have an acceptable arrangement for aligning the lenses on the bodies or frames of the face mask and goggle systems. It would be advantageous to have a simple and effective arrangement for aligning the lenses on the bodies or frames of the face mask and goggle systems, and for keeping the lenses aligned during use.

Accordingly, there is the need for a face mask and/or goggle system that has improved efficacy in keeping projectile materials from passing between the lens or body of the face mask and/or goggle.

There is further the need for a face mask and/or goggle system that includes a means for firmly attaching the lenses to the bodies or frames of the face mask and/or goggle system, while still permitting easy removal and replacement.

There is even further the need for a face mask and/or goggle system that includes a means for aligning the lenses on the body or frame of the face mask and/or goggle system.

SUMMARY OF THE PRESENT INVENTION

A protective face mask system according to the present invention comprises a flexible mask body including an opening for receiving a lens, nose portion, a central portion positioned to the rear of and extending at least partially above the nose portion, a central receiving slot located between the nose portion and the central portion, right and left temple portions, each temple portion having a shaped receiving opening therethrough, left and right cheek portions, and at least one groove located adjacent one of the left and right cheek portions. A transparent flexible lens is provided sized to be received upon and cover the lens opening. The lens includes right and left temple portions including openings therein positioned to correspond to and align with the openings of the mask body when the lens is positioned for attachment to the mask body. The lens including at least a portion that snappingly engages the groove when a portion of the lens is inserted into the slot.

Fasteners are provided for securing the lens to the mask body. The fasteners are preferably two-piece elements, each including a retaining element and a corresponding retaining clip. The retaining element includes a retaining extension that inserts through the lens opening and the corresponding opening in the mask body. The retaining clips include an opening including a cam surface. Rotating a retaining clip at least about a quarter turn about the retaining extension secures the lens to the mask body through the camming action of the relative movement of the retaining clip and the retaining extension.

In an alternate embodiment of the present invention, locking tabs are provided. These locking tabs act as clamps that secure the retaining clips in place when the retaining clips are rotated to a secured or locked position.

DESCRIPTION OF THE INVENTION

Figure 1:
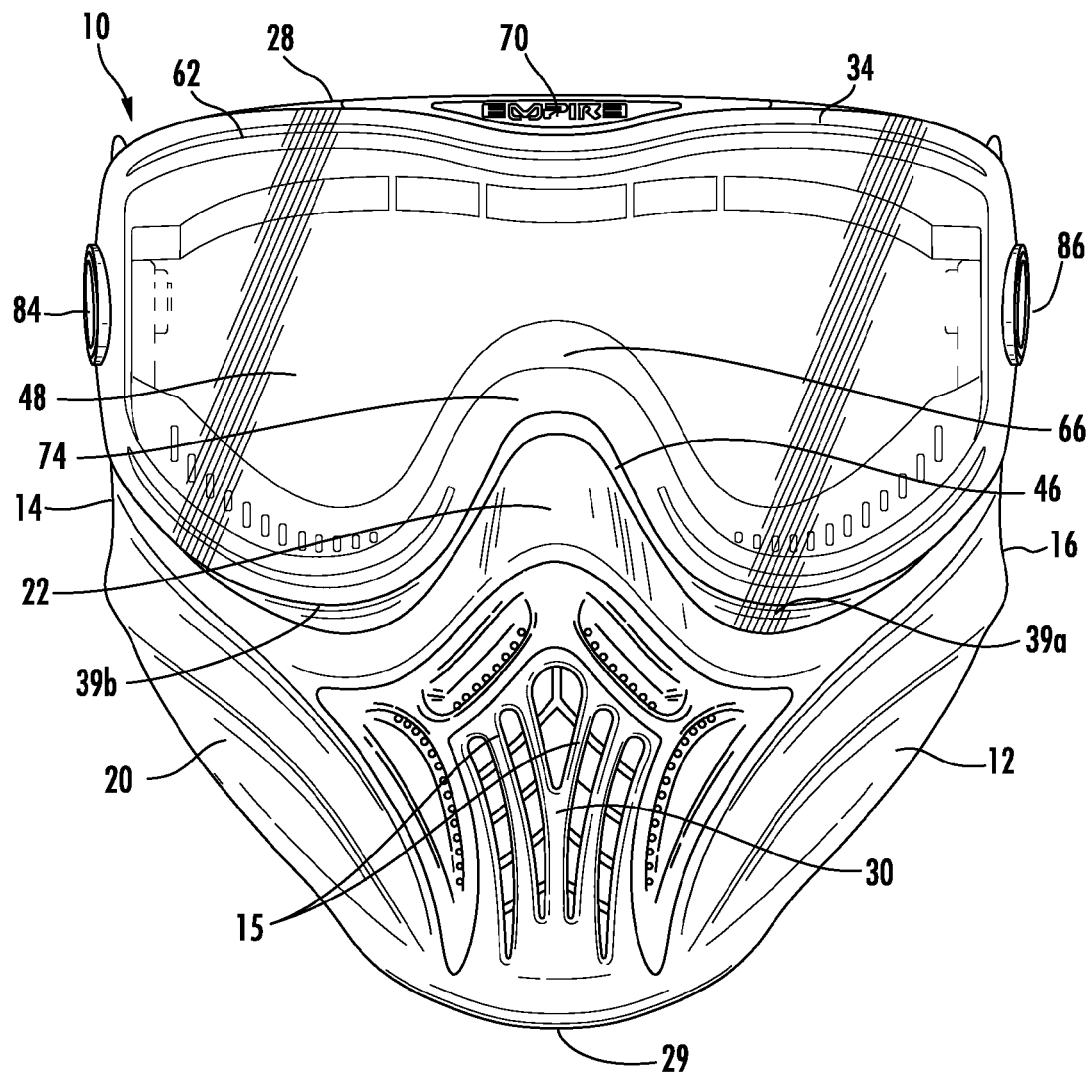
FIG. 1 shows a front view of a face mask system according to the present invention, with the lens assembled on the mask body.

The present invention is directed to a novel face mask and lens arrangement, that provides increased protection to a user, and can be easily assembled or disassembled. In another embodiment, the present invention is directed to a goggle and lens system. The protective face mask 10 is described herein with the right side 14 and left side 16 from the perspective of a user wearing the face mask 10, with each side 14, 16 being essentially a mirror image of the opposite side. The inner side (or inner surface) 18 is that side facing a user wearing the face mask 10, and the outer side 20 is that side facing away from the user.

As shown in FIGS. 1-4 and 20, a face mask 10 according to the present invention includes a mask body 12, having a nose portion 22, opposite temple portions 24 (left side), temple portions 26 (right side), an upper portion 28, and a mouth portion 30. The mask body 12 is formed from a semi-rigid or flexible material, such as a rubber or plastic, or other acceptable material as is known in the art. Preferably, the mask body 12 is formed from a flexible plastic, whereby the mask body 12 may be deformed to allow and/or assist in the attachment and/or detachment of the lens 48, as discussed in greater detail below. The mask body 12 may have various vents 15 for air circulation.

Figure 8:
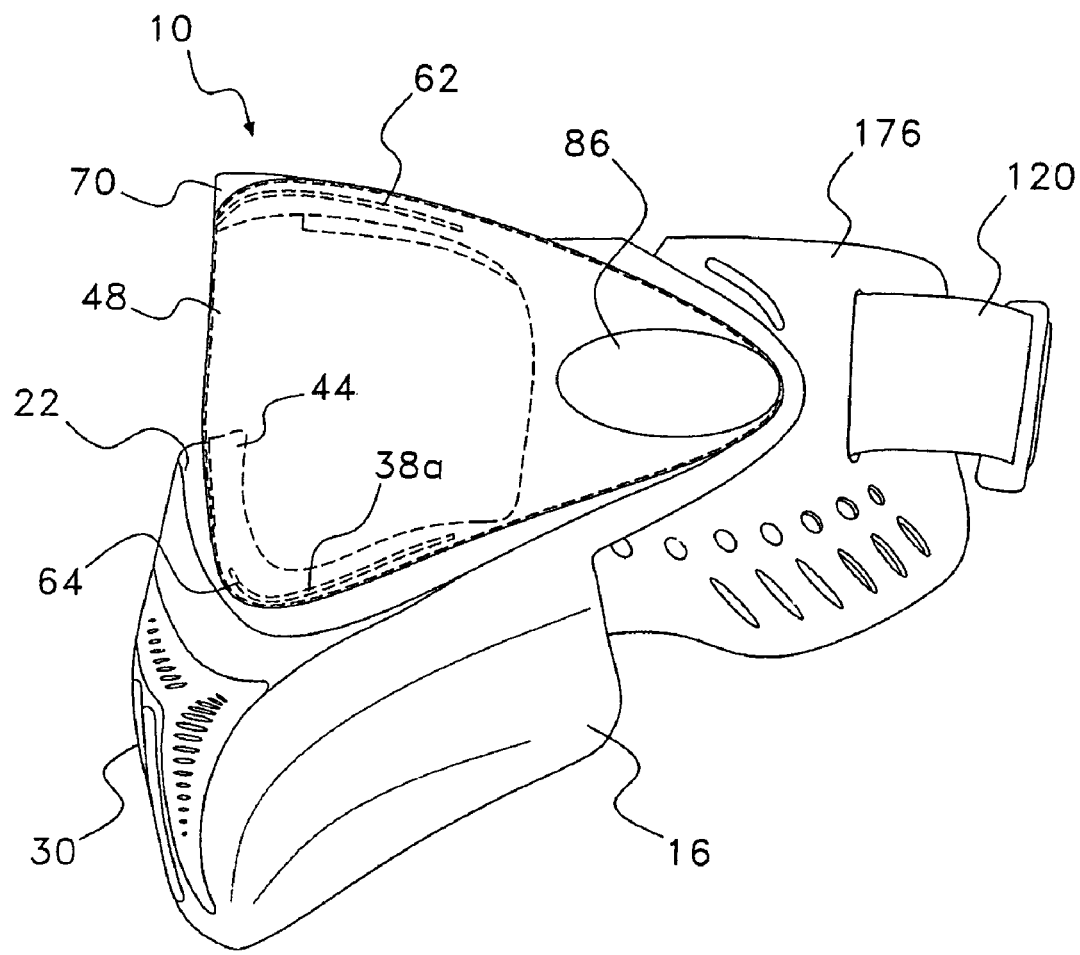
FIG. 8 shows a left side perspective view of an embodiment of an assembled face mask according to the present invention.

FIG. 8 shows an alternate embodiment of the face mask system 10 of the present invention. The side portions, the left side 16 of which is shown in FIG. 8, may include an elastic ear piece portion 176, that a strap 120 attaches to. The elastic ear piece portion 176 can be formed from NEOPRENE, latex, foam, or other materials that are comfortable to a user, and also provide cushioning an support.

Figure 20:
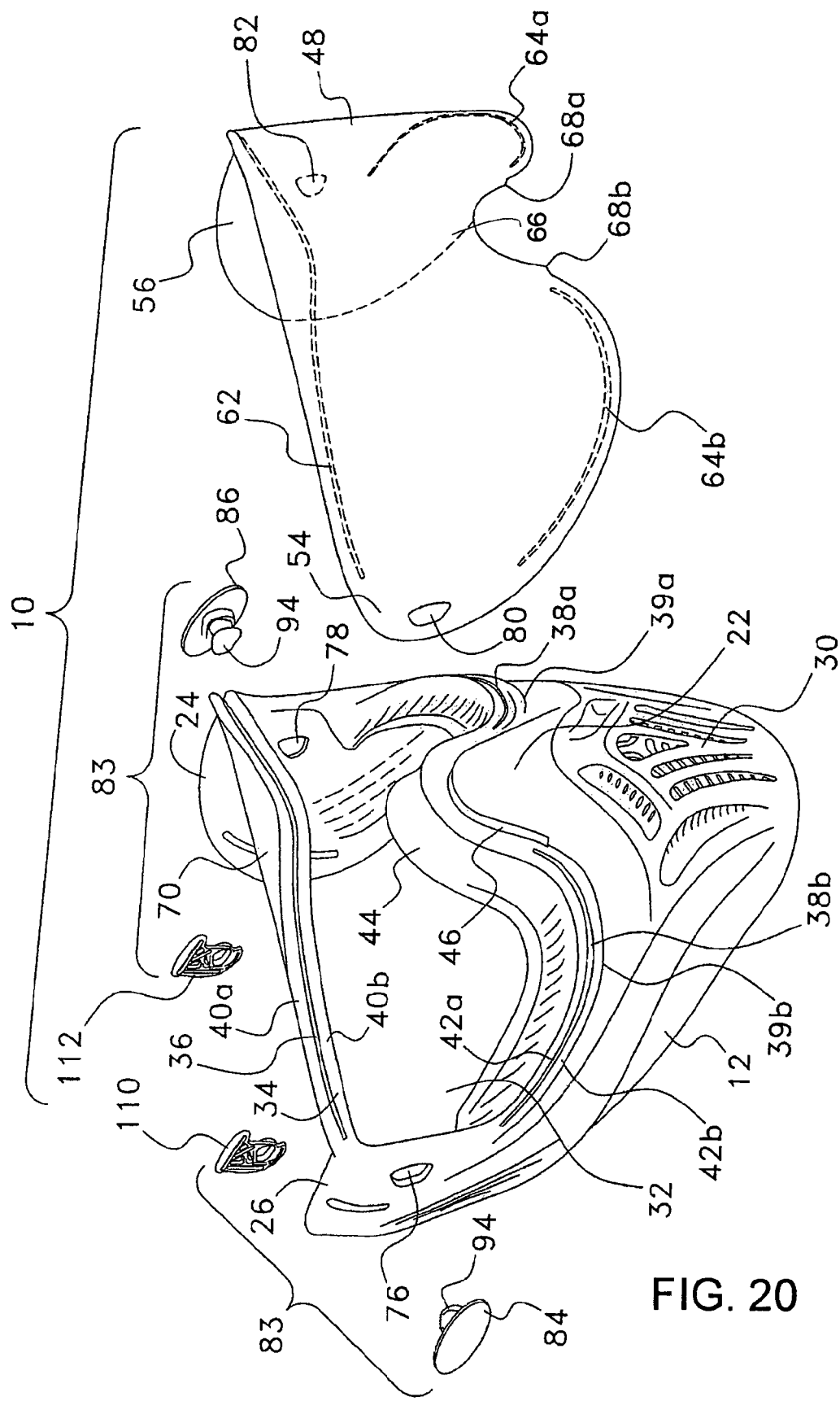
FIG. 20 shows an exploded perspective view of an embodiment of the face mask system of the present invention.
Figure 21:
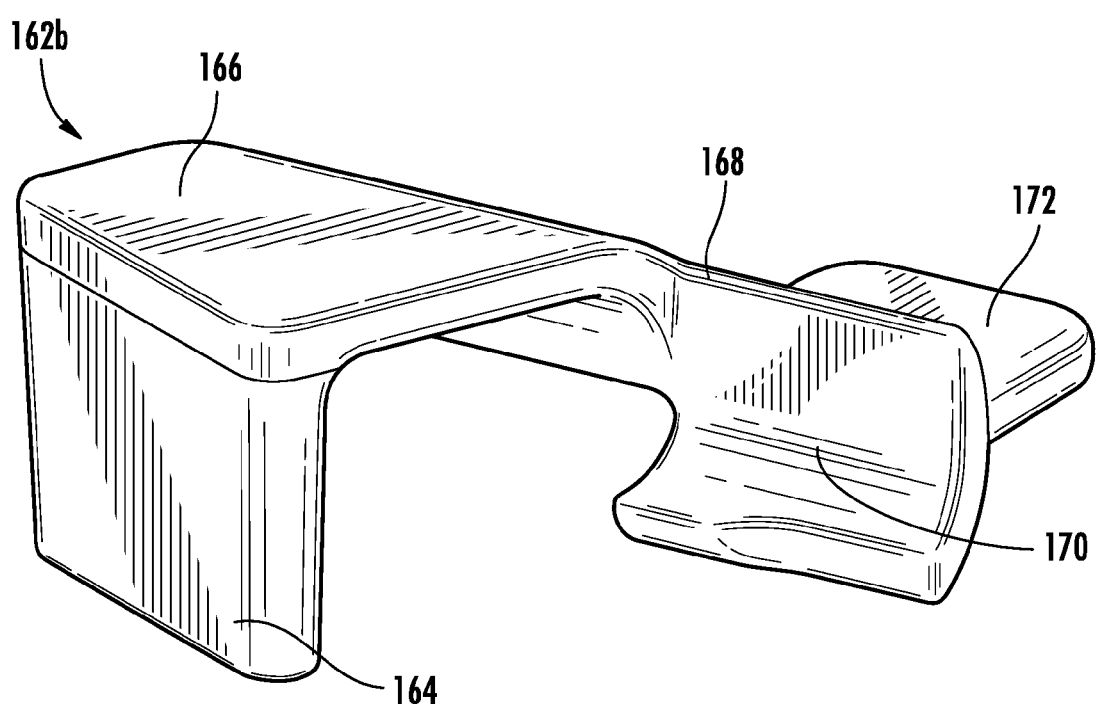
FIG. 21 shows a perspective view of a locking tab of the present invention.
Figure 22:
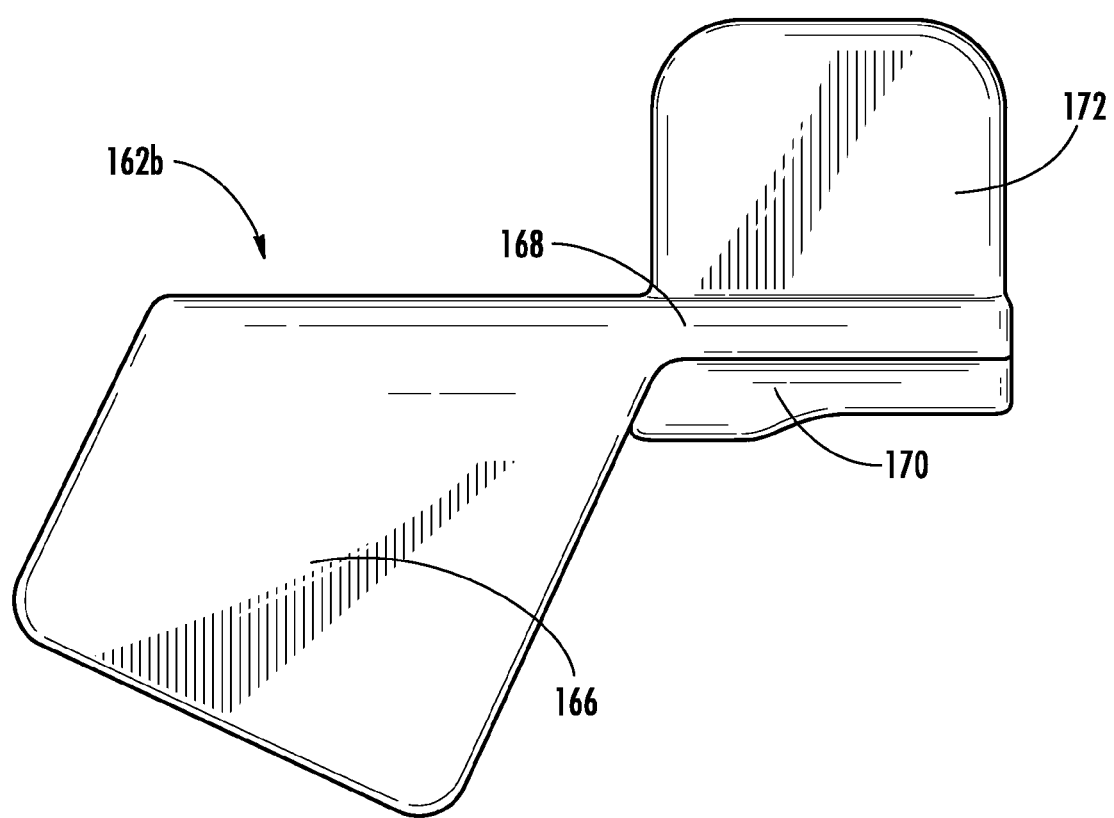
FIG. 22 shows a side perspective view of the locking tab shown in FIG. 22.
Figure 23:
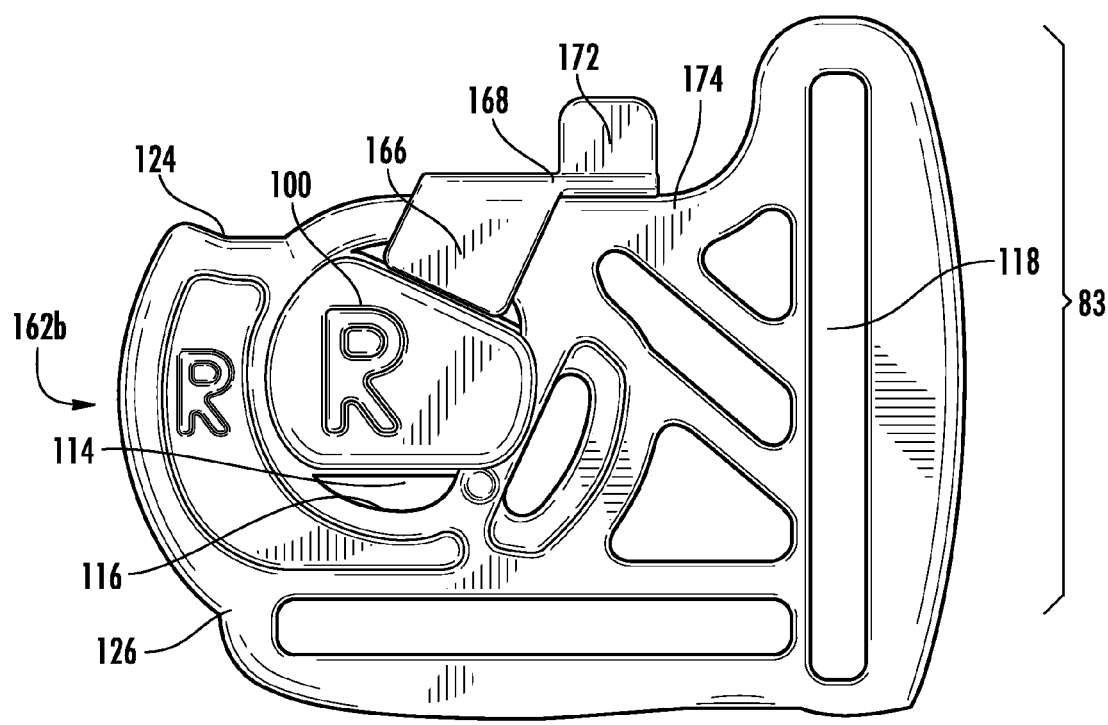
FIG. 23 shows a side perspective view of a right side retaining clip in a locking position about a right side retainer, with the locking clip of FIG. 21 inserted in a locking position.
Figure 24:
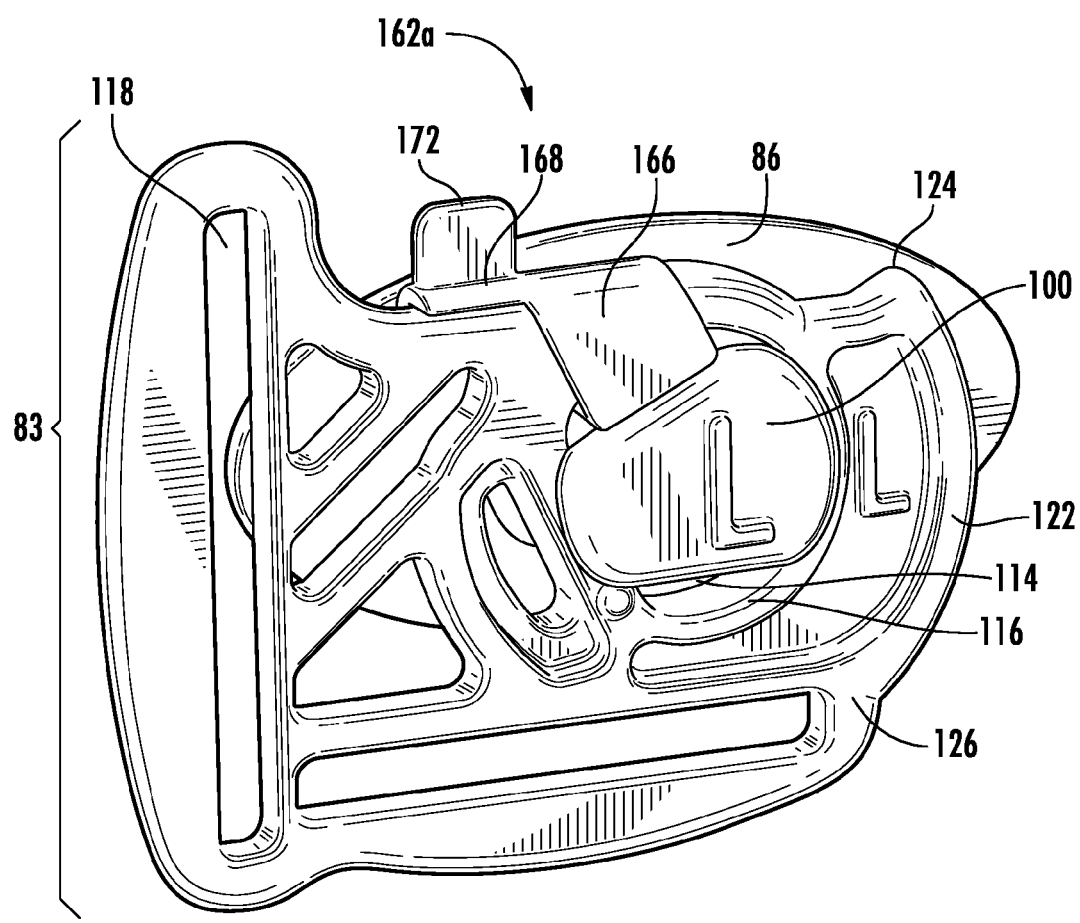
FIG. 24 shows a perspective view of a left side retaining clip in a locking position about a left side retainer, with a left locking clip inserted in a locking position.

A lens opening 32, having right 32r, left 32l, upper 32t and lower 32b portions, is provided for covering by the lens 48 for protecting the eyes of a user. The lens 48 is preferably a one-piece molded plastic at least partially transparent lens that is flexible and can be bent or flexed to a certain degree, but is generally rigid. As shown in FIG. 4, a lens supporting portion 34 runs adjacent the perimeter of the lens opening 32, and may include at least one upper receiving groove 36 and at least one lower receiving groove 38 running along upper and lower portions of the lens supporting portion 34, as shown in FIGS. 4 and 20. The upper groove 36 preferably runs along the outer side 20 of the mask body 12 adjacent the upper portion 28, as shown in FIGS. 1-4, and 20. The lower groove 38 is preferably formed as left lower groove 38a and right lower groove 38b. The left lower groove 38a is provided adjacent the left cheek area 39a of the mask body 12, and the right lower groove 38b is provided adjacent the right cheek area 39b of the mask body 12. Each lower groove 38a, 38b extending from the respective adjacent temple portion 24, 26 to adjacent the nose portion 22, as shown in FIGS. 1-4.

As shown in FIGS. 4 and 20, the upper groove 36 and the lower grooves 38a, 38b may be formed as channels defined by channel walls 40a, 40b, 42a, 42b. For example, channels walls 40a, 40b may be formed in the mask body 12 running along the periphery of the upper groove 36. Similarly, channel walls 42a and 42b may be formed in the mask body 12 running along the periphery of the left lower groove 38a, as shown in FIGS. 1 and 20, and channel walls 42c and 42d may be formed in the mask body 12 running along the periphery of the right lower groove 38b.

Figure 3:
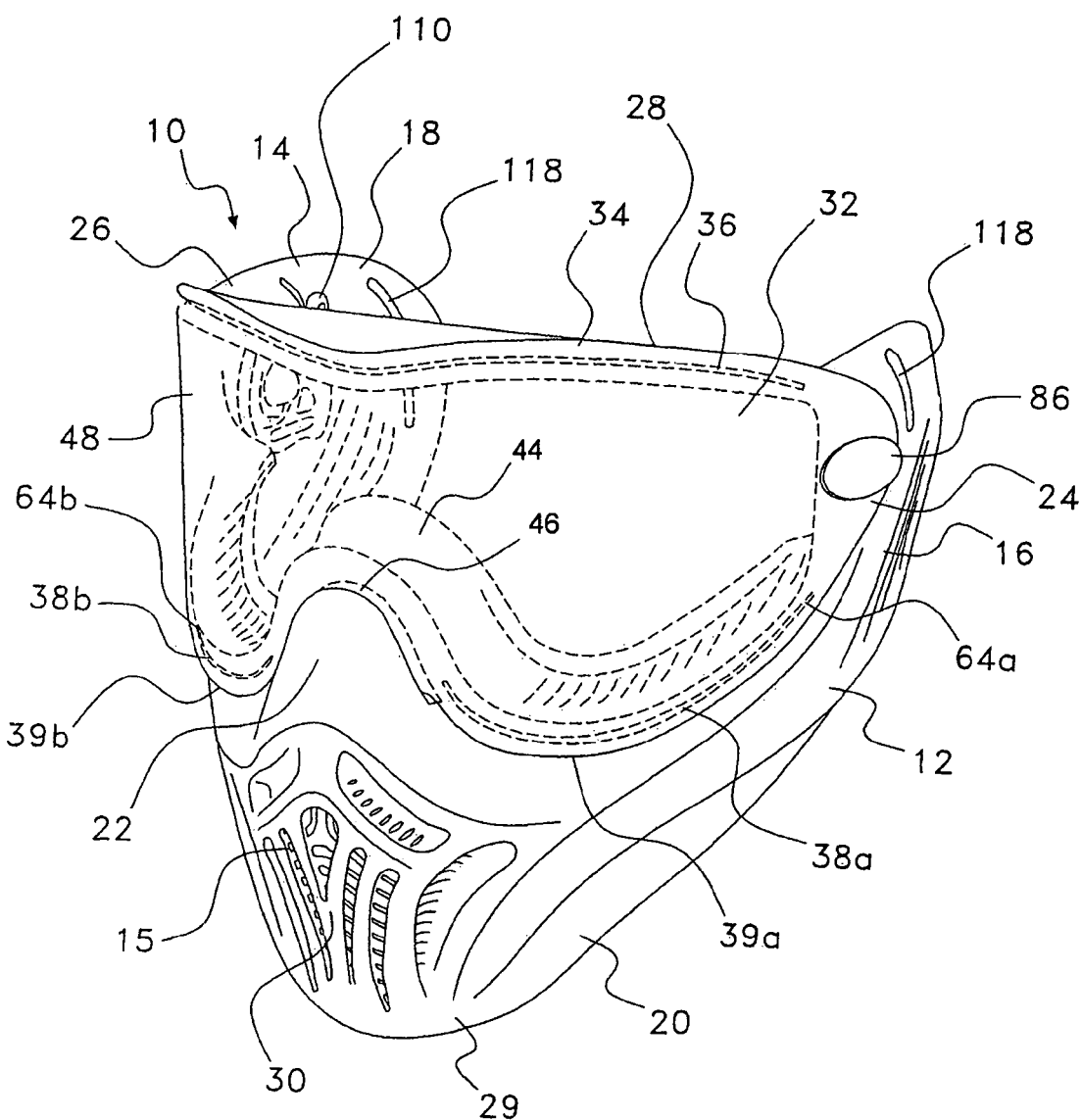
FIG. 3 shows a perspective view of a face mask system according to the present invention from the front left, with the lens assembled on the mask body.
Figure 4:
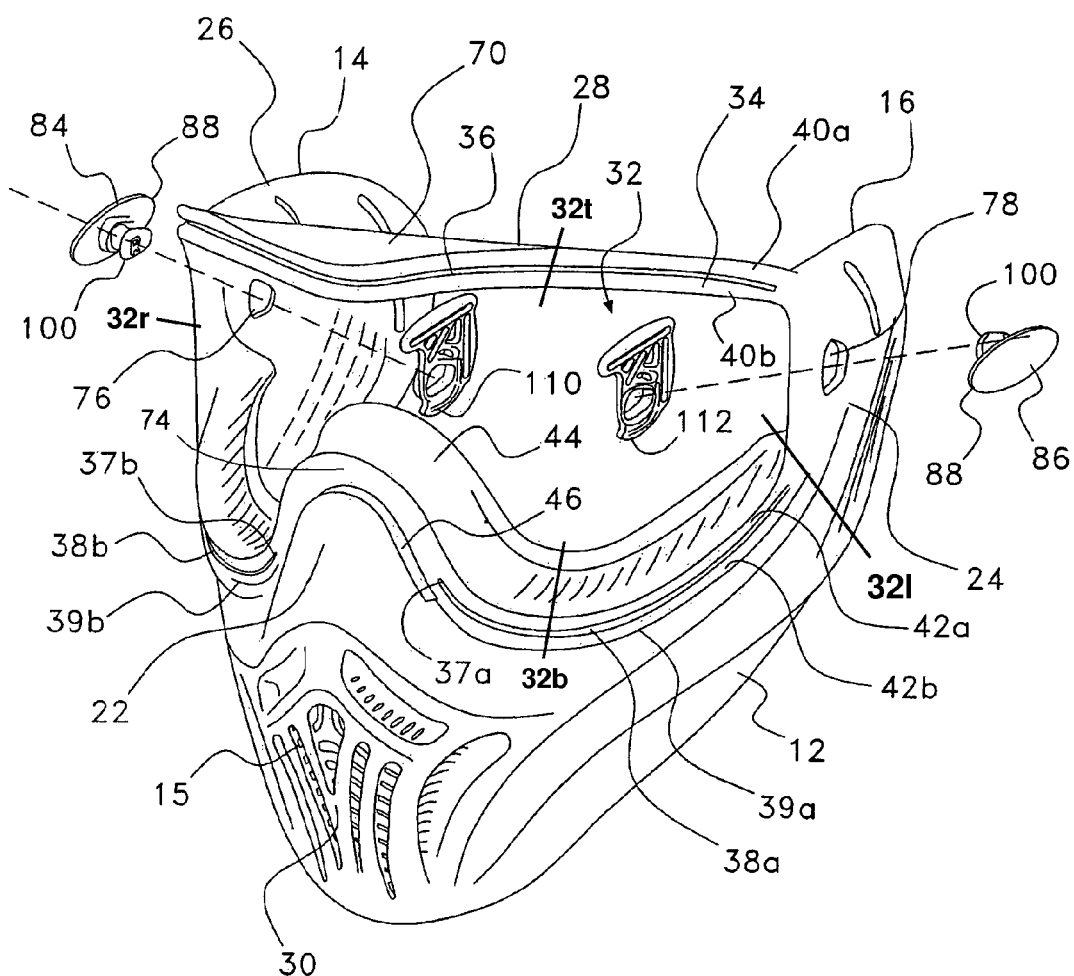
FIG. 4 shows a perspective view of a face mask system according to the present invention from the front left, with the lens removed, showing the insertion of fasteners into the mask body.

The mask body 12 has a central portion 44 adjacent the lens supporting portion 34 which is raised above the nose portion 22, as shown in FIGS. 3, 4 and 20. A central receiving slot 46 is provided between the central portion 44 of the lens supporting portion 34 and the nose portion 22. The central receiving slot 46 extends downwardly relative to the normal orientation of the mask 10 as a U-shaped channel in the mask body 12. The central receiving slot 46 provides an opening for receiving the lens 48 between the central portion 44 and the nose portion 22, as described in greater detail below. The width of the central receiving slot 46 is approximately about the width of the lens 48. Preferably, the width of the central receiving slot 46 is slightly smaller than the width of the lens 48.

Figure 5:
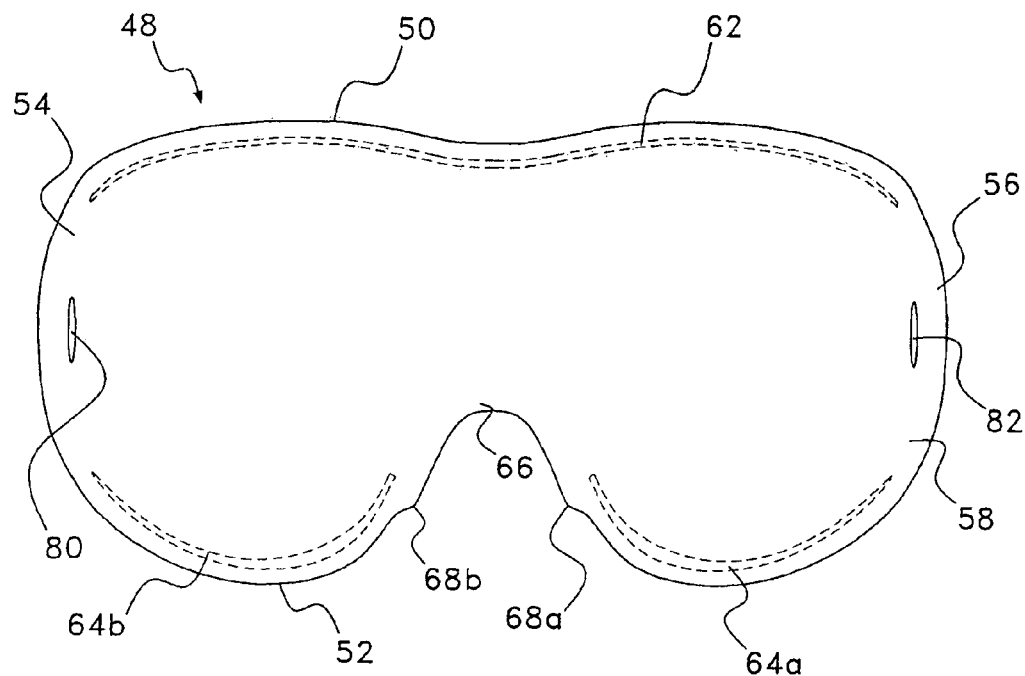
FIG. 5 shows a front view of a lens for the face mask system of the present invention.
Figure 6:
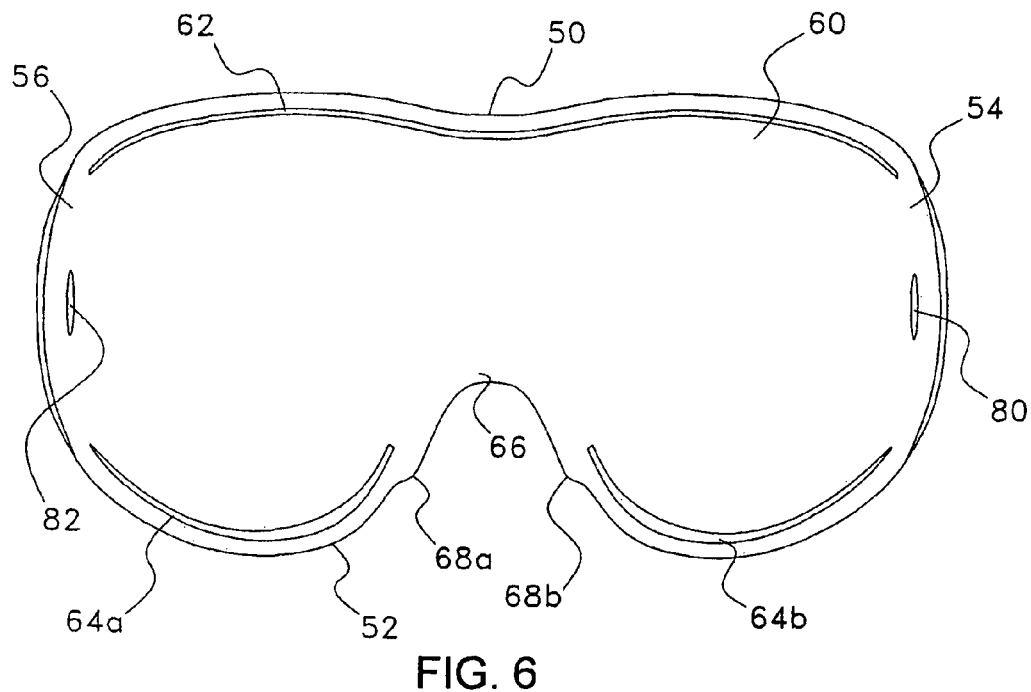
FIG. 6 shows a back view of the lens shown in FIG. 6.
Figure 7:
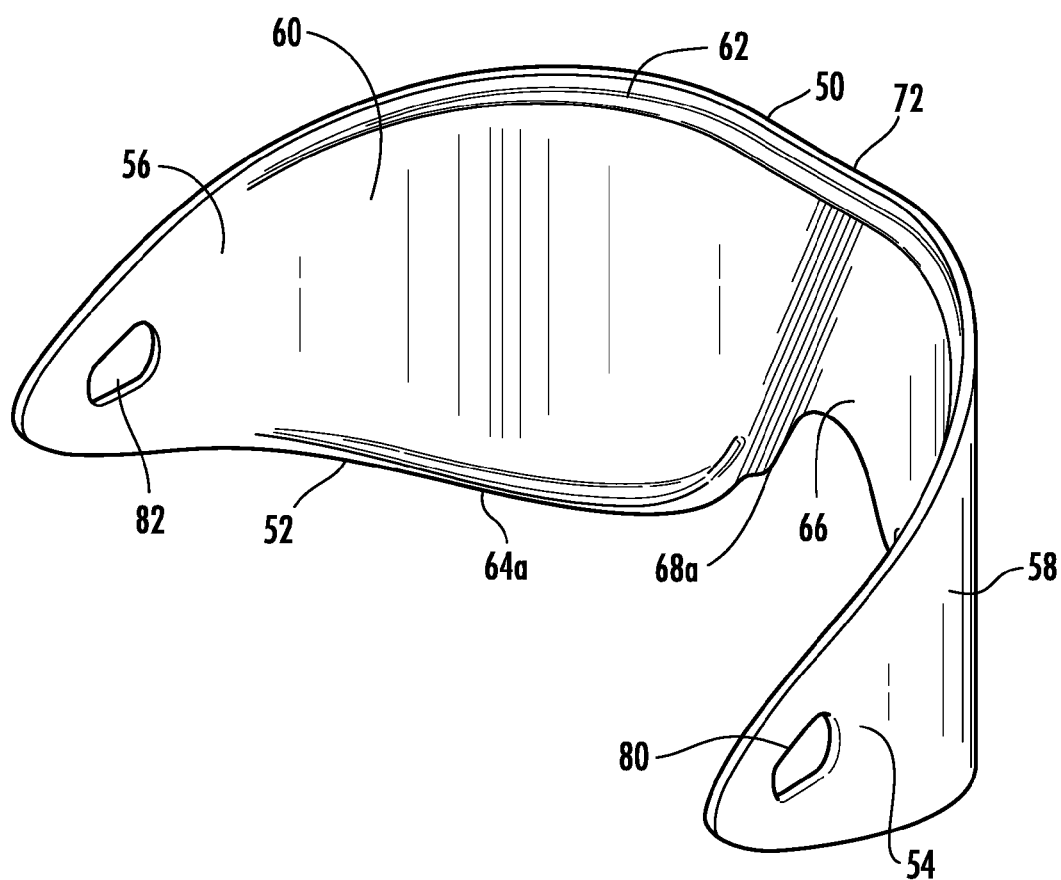
FIG. 7 shows a perspective view from the right rear of the lens shown in FIG. 6.

As shown in FIGS. 5-7, a single piece lens 48 is provided for covering the lens opening 32, and providing protection to a user's eyes, and for preventing the passage of, for example, paintballs during a paintball sport game or match. The lens 48 has an upper portion 50, a lower portion 52, a right temple portion 54, a left temple portion 56, an outer surface 58, an inner surface 60, and a nose portion 66. The lens 48 further comprises two nose extensions 68a (left) and 68b (right), extending adjacent the nose portion 66 of the lens 48, as shown in FIGS. 5-7. Preferably, the lens 48 is larger than the lens opening 32, so that the lens 48 covers and preferably overlaps the lens receiving portion 34 and rests against the mask body 12 when attached.

The lens 48 includes at least one upper flange 62 (or tongue, lip, rib or rim) adjacent to the upper portion 50 of the lens 48 and extending along the inner surface 60 of the lens 48 substantially between the right temple portion 54 and the left temple portion 56, as shown in FIGS. 6 and 7. The lens further includes at least one lower flange 64 (or tongue, lip, rib or rim) adjacent the lower portion 52 of the lens 48 and running along the inner surface 60 of the lens. The lower flange 64 is preferably formed as separate lower left flange 64*a* and a lower right flange 64*b*, as shown in FIG. 6, extending along at least a portion of the length of the inner surface 60 of the lens 48 along the lower portion 52.

The upper flange 62 is formed to correspond to the receiving groove 36, and the lower flanges 64*a*, 64*b* are formed to correspond respectively to the lower grooves 38*a*, 38*b*. The upper flange 62 will engage the receiving groove 36, and the lower flanges 64*a*, 64*b* will engage the receiving grooves 38*a*, 38*b* when the lens 48 is in an attached position. The flanges 62, 64*a*, 64*b* may be formed to snap into the respective receiving grooves 36, 38*a*, 38*b* when the when the lens 48 is in an attached position, such as when the nose portion 66 of the lens 48 is inserted into the central receiving slot 46.

Preferably, the flanges 62, 64*a*, 64*b* are sized and shaped to be received in the receiving grooves 36, 38*a*, 38*b* in such a manner that the flanges 62, 64*a*, 64*b* and receiving grooves 36, 38*a*, 38*b* act to assist in aligning the lens 48 on the lens supporting portion 34 of the mask body 12, and further assist in preventing slippage or movement of the lens 48 relative to the mask body 12 when in use.

The mask body 12 may be formed from a flexible or pliable plastic, or any other similar material or material having similar properties, so that portions of the mask body 12 may be flexed, or the entire mask body may be flexed. The material of the mask body 12 should be selected so that it is sufficiently rigid and impact resistant to provide protection to a user when worn, and is also flexible but will return to substantially its original shape when released from flexing. For example, with the mask body 12 formed from a flexible material, opposing sides 14, 16 may be brought closer to each other, deforming the shape of the mask body 12. Portions of the mask body 12 in the area of the central portion 44, nose portion 22, cheek portions 39*a*, 39*b*, and adjacent the grooves 38*a*, 38*b*, may be flexed when the opposing sides 14, 16 are brought closer to each other.

Figure 9:
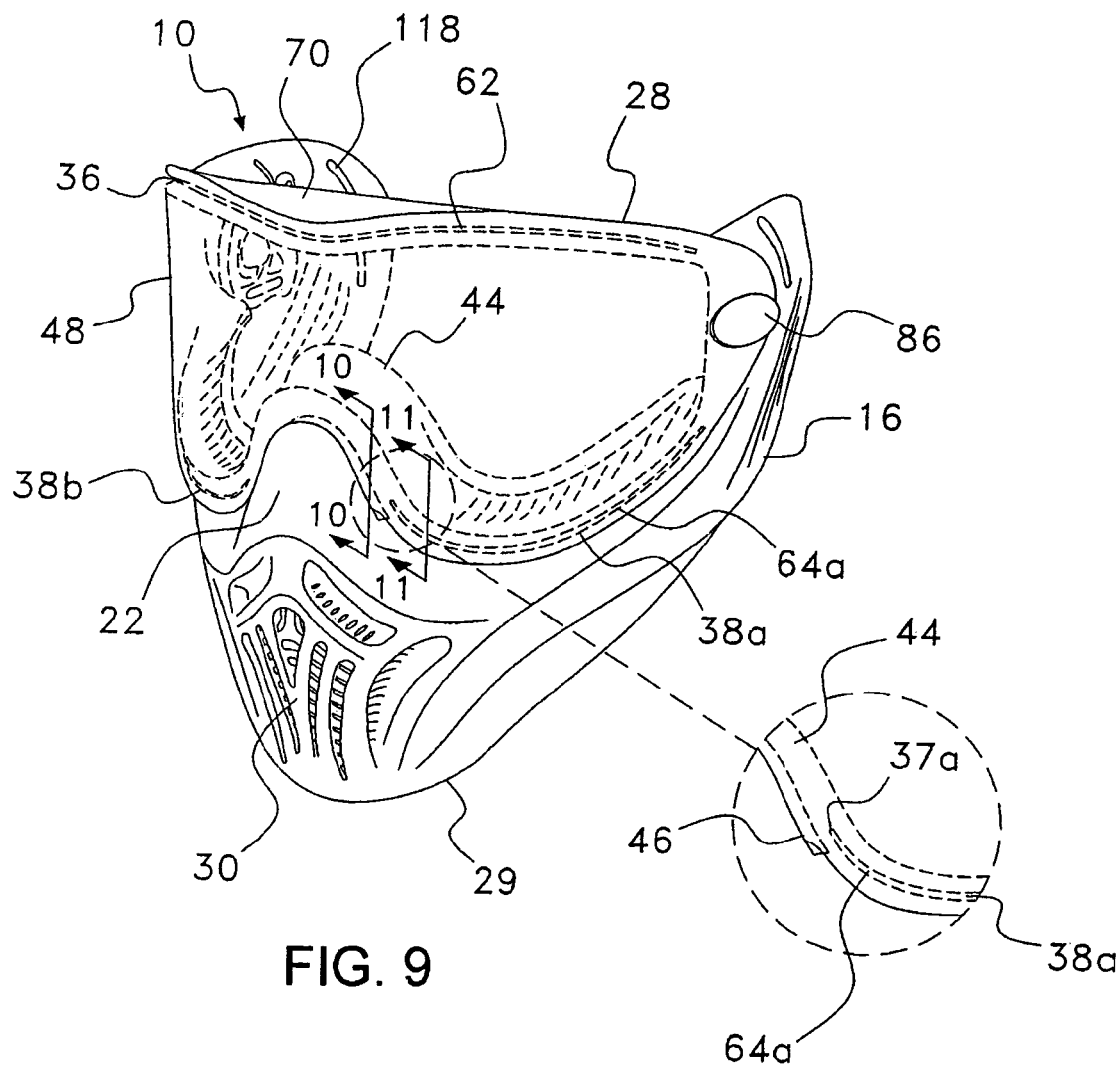
FIG. 9 shows a perspective view from the front left of a face mask system according to the present invention.
Figure 9A:
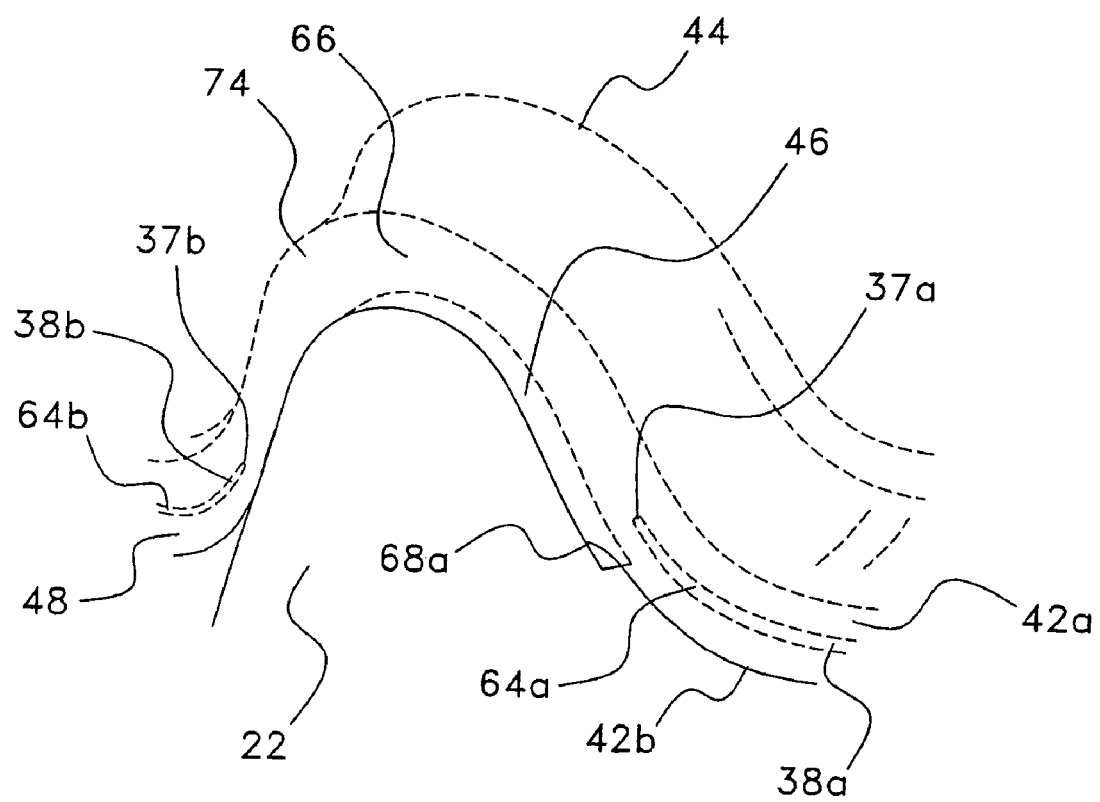
FIG. 9A shows a close up view of the nose portion, central receiving slot, and central portion of the mask body and lens of the present invention shown in FIG. 9.
Figure 11:
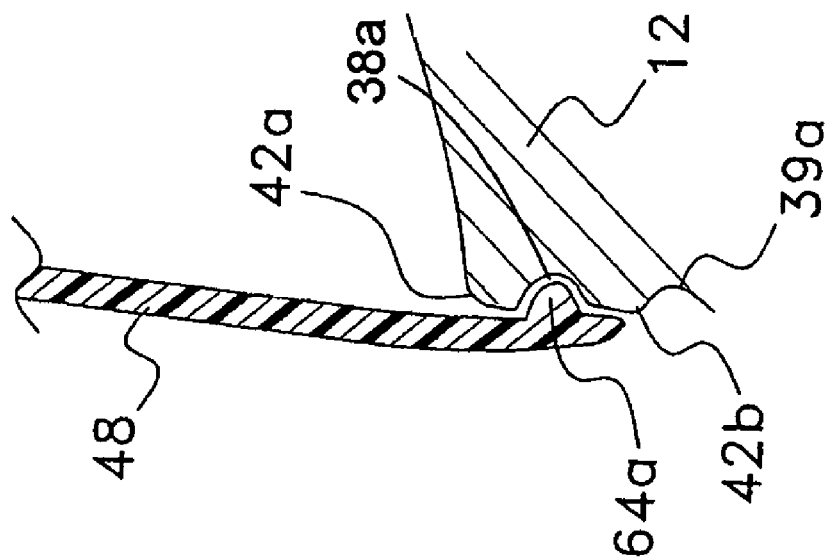
FIG. 11 shows a cross sectional view taken along line 11-11 in FIG. 9, showing a left lower flange of the lens engaging a left lower groove of the mask body.

In particular, when the opposing sides 14, 16 are brought closer together, deforming the mask body 12, the cheek portion 39*a*, 39*b* areas adjacent the middle ends 37*a*, 37*b* of the grooves 38*a*, 38*b* and area surrounding the central portion 44, and nose portion 22 are flexed. When the mask body 12 is sufficiently flexed, at least a portion of the nose extensions 68*a* and/or 68*b* and/or a portion of the nose portion 22 are positioned at least partially within the central receiving slot 46, and the combined thickness of the flanges 64*a*, 64*b* of the lens 48 and the lens 48 are permitted to pass snappingly into the grooves 38*a*, 38*b*, as shown in FIGS. 11. The area where snapping engagement will generally initially and most substantially take place is shown in detail in FIG. 9*a*, adjacent the middle portions 37*a*, 37*b* of the lower grooves 64*a*, 64*b*, as the depicted area is closest to the nose portion 22, central receiving slot 46 and central portion 44, and will be flexed to a lesser degree than the other portions of the mask body 12.

Figure 10:
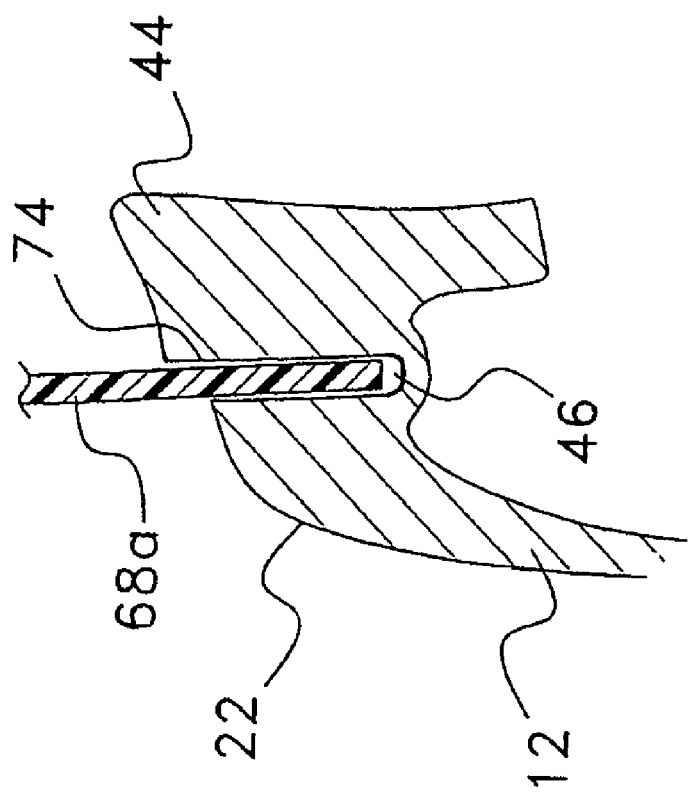
FIG. 10 shows a cross sectional view taken along line 10-10 in FIG. 9, showing a nose extension section of the lens in a central receiving slot in the mask body.

When the flanges 64*a*, 64*b* are snapped into place, such as between flexed channel walls 40*a*, 40*b*, and 42*a*, 42*b*, the nose portion 22 and nose extensions 68*a* and 68*b* of the lens 48 are seated in the central receiving slot 46, as shown in FIG. 10. When the mask body 12 is permitted to return to its original (non-flexed or non-deformed) shape, the portions of the flanges 64*a*, 64*b* of the lens 48 that have not snapped into place are now aligned, and will engage the grooves 38*a*, 38*b*, while the nose portion 66 and nose extensions 68*a* and 68*b* will be held within the central receiving slot 46. The lens 48 is now positioned firmly about the lens supporting portion 34 of the mask body 12.

It is preferable that the width of the central receiving slot 46 is sized (in its non-flexed or non-deformed state) to be about the thickness of the lens 48. When the mask body 12 is flexed such as by moving the opposing sides 14, 16 closer to each other, and the central portion 44 and area adjacent the grooves 38*a*, 38*b* is flexed or deformed. With the nose portion 66 of the lens 48 in the receiving slot 46, the flanges 64*a*, 64*b* can pass by the surface of the area adjacent the grooves 38*a*, 38*b*, such as channel walls 40*a* and 40*b*, into the receiving grooves 38*a*, 38*b*. Once the flanges 64*a*, 64*b* snap into place in the grooves 38*a*, 38*b*, the nose portion 22 and nose extensions 68*a*, 68*b* can drop further into and be seated in the central receiving slot 46. The nose extensions 68*a*, 68*b* are supported at or adjacent to the bottom of the slot 46, as shown in FIG. 10. This provides a firm locking or snapping engagement of the nose portion 22 and flanges 64*a*, 64*b* into the mask body 12. Releasing the mask body 12 and allowing it to return to its non-deformed, non-flexed, normal state provides an even tighter engagement of the full length of the flanges 64*a*, 64*b* with the receiving grooves 38*a*, 38*b*. It is preferred that a user would not be able to remove the lens 48 from its engagement with the mask body without flexing or otherwise deforming the mask body 12.

This engagement further assists in fixing the lens 48 in place when in use. It is appreciated that, due to the design of the present invention, this arrangement will firmly hold the lens 48 in place on the mask body 12. The face mask system 10 of the present invention comprises even further means for maintaining the lens in place attached to the mask body, as discussed below.

As shown in FIGS. 1-4, a central portion 70 of the upper portion 28 may extend or otherwise slope downward, and engage a receiving portion 72 in the middle of the upper portion 50 of the lens 48. The upper flange 62 of the lens 48 is received within the upper receiving groove 36. Because the mask body 12 is formed from a flexible material, the upper flange 62 of the lens 48 can additionally snap into the upper receiving groove 36. This provides an additional alignment means for maintaining the lens 48 in the correct position on the mask body 12.

According to a further feature of the present invention, the central portion 44 of the lens supporting portion 34 is formed so that, in its normal orientation, the central portion 44 is higher than (raised or above) the nose portion 22, as shown in FIGS. 4 and 20. The central portion 44 may be formed having a central support wall 74, which is a generally flat, U-shaped surface against which the nose portion 66 of the lens 48 can rest and/or be supported by from the rear. Thus, the lens 48 is supported from behind by the central portion 44 and central support wall 74 when the lens 48 is attached to the mask body 12, such as when the nose extensions 68*a* and 68*b* are engaged with the central receiving slot 46. This provides a novel and effective arrangement that prevents the lens 48 from displacing in relation to the mask body 12 if impacted by a projectile. If, for example, a projectile (such as a paintball) were to impact the lens 48 adjacent the nose portion 22 of the mask body 12 or the nose portion 66 of the lens 48, the mask body 12 and lens 48 will not separate. The lens 48 will be supported from behind by the central support wall 74, and the mask body 12 will not be moved away from the lens 48 or otherwise create a penetrable space or opening. The lens 48 is also supported within the slot 46 at its front by the nose portion 22. The arrangement of the present invention prevents the lens 48 from moving or otherwise being dislodged along its edges, as the nose extensions 68*a* and 68*b* are held within the central receiving slot 46, and the upper flange 62 and the lower flanges 64*a*, 64*b* engage the respective receiving grooves 36 and 38*a*, 38*b*.

To provide further engagement of the mask body 12 and the lens 48, the mask body 12 is formed having a right receiving opening 76 located adjacent the right temple portion 26, and a left receiving opening 78 located adjacent the left temple portion 24, as shown in FIGS. 4 and 20. The lens 48 includes a corresponding respective right receiving opening 80 and left receiving opening 82, as shown in FIGS. 5-7. The openings 76, 78, 80, 82, are shaped and positioned to be in alignment when the lens 48 is attached to the mask body 12, with the right temple portion 54 of the lens 48 overlapping a part of the right temple portion 26 of the mask body 12, and the left temple portion 56 of the lens 48 overlapping a part of the left temple portion 24 of the mask body 12.

In order to affix the lens 48 to the mask body 12 adjacent the temple portions 24, 26, fasteners 83 are provided. In particular, the fasteners 83 are preferably provided as two-piece elements, including a right retaining element 84 and a left retaining element 86, and corresponding respective right retaining clip 110 and left retaining clip 112. In general, the face mask system 10 of the present invention is designed so that the lens 48 is securely and/or lockingly engaged to the mask body 12 by a fastener 83 that includes at least a portion which is rotated at least about a quarter turn relative to the mask body 12 and lens 48 to secure the lens to the mask body. This provides for fast and efficient attachment and detachment of the lens 48 to and from the mask body 12. Unlike known goggle or mask systems, the present invention provides for retaining elements that lock the lens 48 on the mask body 12 by moving the retaining elements by approximately at least about a quarter turn, or approximately at least about ninety degrees. The fasteners 83 are preferably quick-release, cam-locking fasteners that are easily locked and unlocked, and are separable from the lens and mask body.

Figure 12:
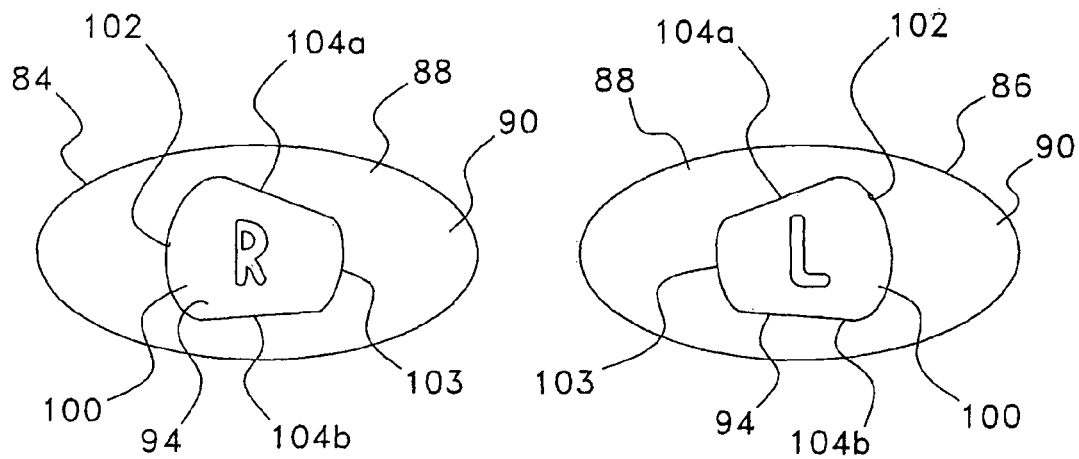
FIG. 12 shows a top plan view of an embodiment of the right and left retainers of the present invention.
Figure 13:
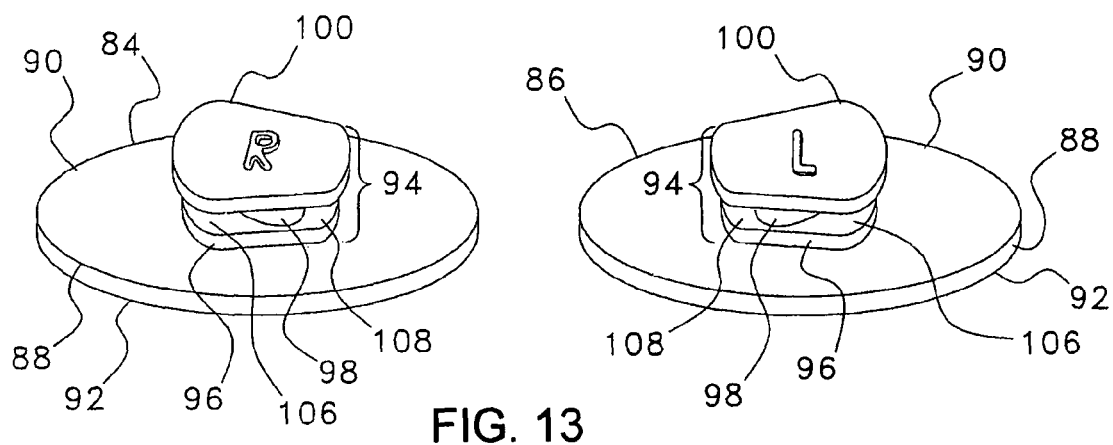
FIG. 13 shows a perspective view of the retainers shown in FIG. 12.
Figure 14:
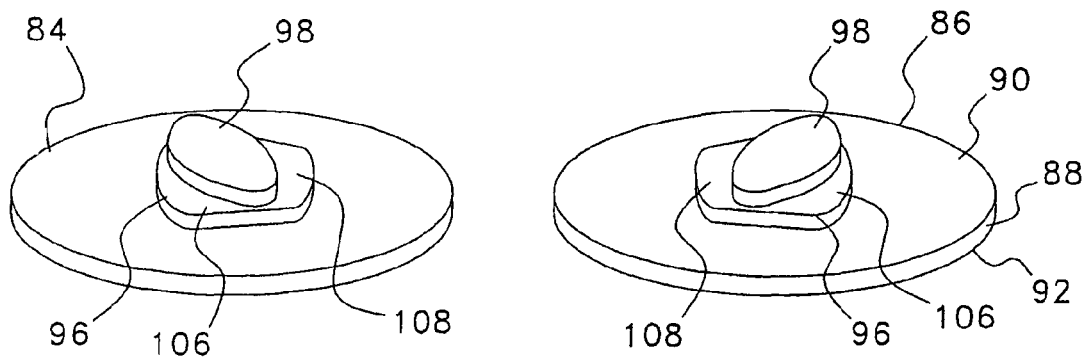
FIG. 14 shows a partial cutaway view of the retainers shown in FIG. 13.

As shown in FIGS. 12-14, each retaining element 84, 86 includes a retaining wall portion 88 having an inner surface 90 and an outer surface 92. Each retaining wall portion 88 is preferably ovoid in shape, although the wall portion 88 can be any shape. A retaining extension 94 extending from the inner surface 90 of the retaining wall portion 88 includes a base 96, a shaped post 98, and a tab portion 100. The base 96 and tab portion 100 each have a generally trapezoidal cross section with rounded edges, as shown in FIGS. 12-14, with a larger portion 102, inwardly sloping walls 104a, 104b and a smaller portion 103 opposite the larger portion 102. Each receiving opening 76, 78, 80, 82 is preferably shaped having a generally trapezoidal cross section with rounded edges corresponding to the shape of the base 96 and tab 100, with each opening 76, 78, 80, 82 sized to be slightly larger than the base 96 and tab 100, such that the base 96 and tab 100 can pass through or alternately fit within each opening 76, 78, 80, 82. The right retaining element 84 and the left retaining element 86 are essentially mirror images of each other, as shown in FIGS. 4 and 20.

The post 98 preferably has a generally ovoid cross section, as shown in FIGS. 13-14. The positioning of the post 98 between the base 96 and the tab 100 provides a first groove 106 and a second groove 108. The first groove 106 and second groove 108 form a cam surface, as described in greater detail below. As shown in FIG. 14, when viewing the right retaining element 84 from the tab 100 side, the post 98 is oriented sloping from adjacent the upper left corner of the base 96 and tab 100, to adjacent the lower right corner of the base 96 and tab 100. The left retaining element 86 provides a mirror image, with the post 98 being oriented sloping from adjacent the upper right corner of the base 96 and tab 100, to adjacent the lower left corner of the base 96 and tab 100.

A right side retaining clip 110 and a left side retaining clip 112 are provided for engaging the right retaining element 84 and the left retaining element 86, respectively, as shown in FIGS. 4, 16-20. The right side retaining clip 110 and a left side retaining clip 112 are essentially mirror images. The retaining clips 110, 112 are preferably generally L-shaped, and each has a generally trapezoidal opening 114 shaped and sized to receive the tab 100. The openings 114 define a cam surface 116 for engaging the posts 98. Strap slots 118 are provided opposite the openings 114. These strap slots 118 are adapted to receive a strap (not shown) that can extend around the rear of the head of a user.

A description of how to secure and remove the lens 48 to and from the mask body 12 will now be provided, using the example of the right temple portion 54 of the lens 58, right temple portion 26 of the mask body 12, right retaining element 84, and right side retaining clip 110, as shown in FIGS. 16-19.

The lens 48 is positioned over the lens opening 32. The mask body 12 is flexed, preferably by bringing the temple portions 24, 26 towards each other. The nose portion 66 of the lens and nose extensions 68a, 68b are inserted into the slot 46. The flanges 62, 64a, 64b, are aligned with and snapped into the grooves 36, 38a, 38b. The openings 76, 78, 80, 82 are aligned, as shown in FIGS. 18-20.

Figure 15:
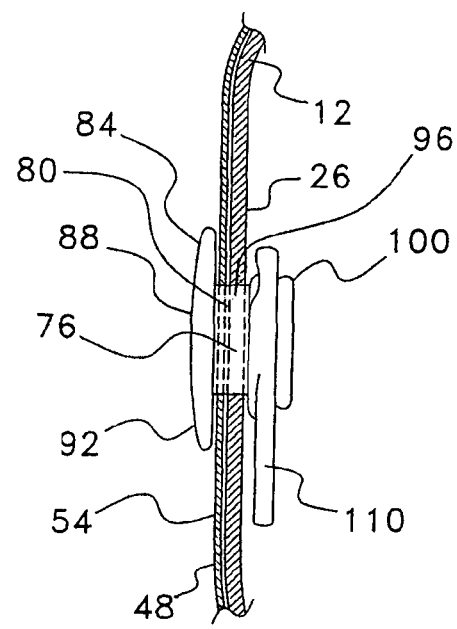
FIG. 15 shows a partial cross sectional view from the front of the right side retaining element inserted into and securing the lens to the mask body with the right side retaining clip.
Figure 18:
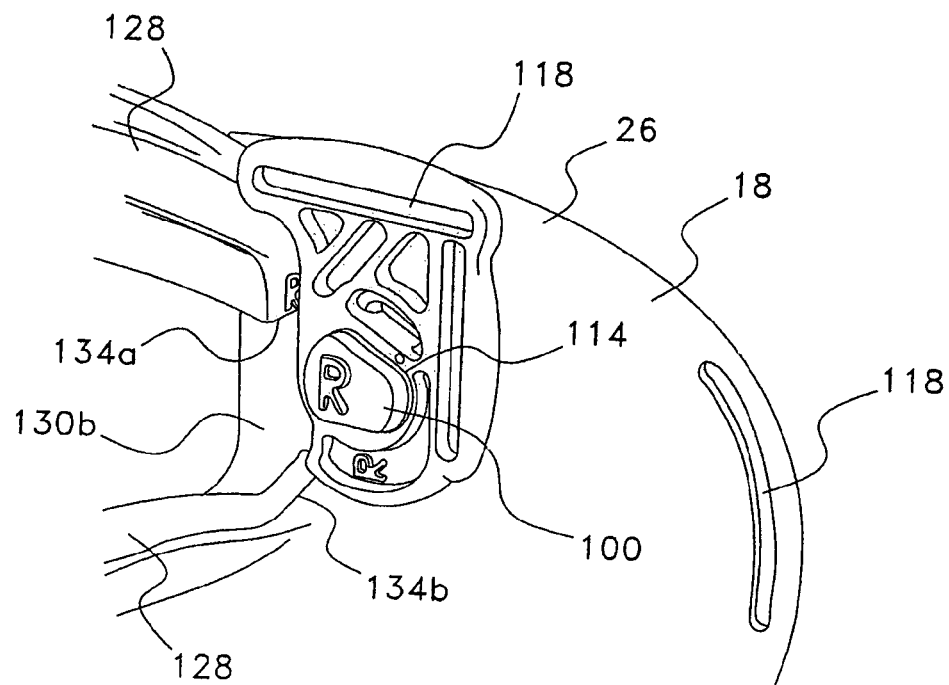
FIG. 18 shows a perspective view of the inner side of the right temple portion of the mask body with a right side retaining clip engaging a right side retainer in the first or unlocked position.
Figure 19:
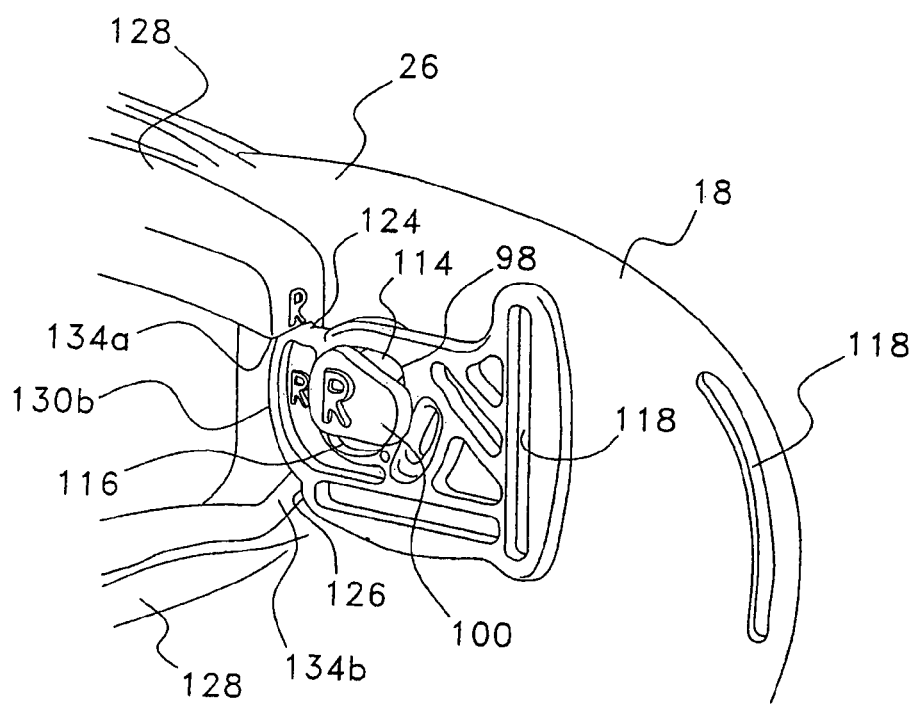
FIG. 19 shows a perspective view of the inner side of the right temple portion of the mask body with a right side retaining clip engaging a right side retainer in the second or locked position.

The right retaining element 84 is inserted through the right receiving opening 80 of the lens 48, and the right receiving opening 76 of the mask body 12, adjacent the temple portion 26 of the mask body 12, as shown in FIGS. 15, 18-19. The retaining extension 94 is preferably sized so that the tab 100 and a portion of the post 98 and extend through the openings 76, 80, and beyond the inner side 18 of the mask body 12. In an preferred embodiment, the base 96 is sized to fit within the openings 76, 80, acting as yet another alignment means, and to keep the lens 48 from moving relative to the mask body 12, as shown in FIG. 15.

Figure 16:
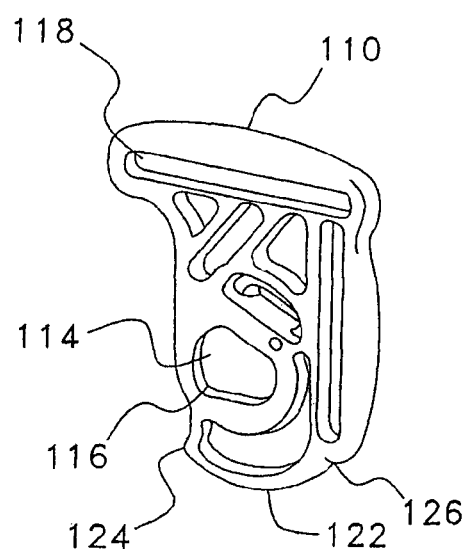
FIG. 16 shows a perspective view of the left side of the right side retaining clip.
Figure 17:
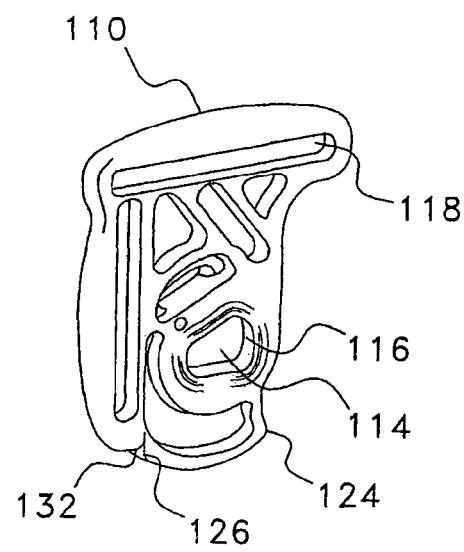
FIG. 17 shows a perspective view of the right side of the right side retaining clip.

The right retaining clip 110 includes an opening 114 that is shaped to match the shape of the tab 100, and is slightly larger than the tab 100, as shown in FIGS. 16-17. The retaining clip 110 is positioned with the tab 100 passing through the opening 114, and the opening 114 aligned with the post 98. The retaining wall portion 88 of the retaining element 84 is positioned against the outer side 20 of the mask body 12, as shown in FIGS. 1 and 3. The retaining clip 110 is positioned against the inner side 18 of the mask body 18 adjacent the right temple portion 26, as shown in FIG. 15.

Due to their respective shapes, the post 98 and opening 114, including the cam surface 116, of the retaining clip 110 provide a cam and locking action to secure the retaining element 84 in place, and thereby secure the lens 48 to the mask body 12. The grooves 106, 108 of the post 98 will preferably only allow the retaining clip 110 to move in one direction, in the example, clockwise when viewing the mask 10 from the inner side 18, when positioned as in FIGS. 18-19. When the retaining clip 110 is turned from a first or "unlocked" position, to a second or "locked" position at approximately about a quarter turn, or approximately about ninety degrees, as shown in FIGS. 18-19, the interaction of the shaped opening 114 and the shaped post 98 provide a secured or locking engagement. The tab 100, post 98 and the retaining clip 110 are sized so that the retaining clip 110 fits firmly between the inner side 18 of the mask 10 and the tab 100, as shown in FIG. 15. Turning the retaining clip 110 as described "sandwiches" the mask body 12 and the lens 48 between the retaining wall 88 and the retaining clip 110 and tab 100, providing securing the lens 48 in place on the mask body 12, as shown in FIG. 15. The left retaining element 86, left retaining clip 112, and left side openings 78, 82, operate as described above, in essentially a mirror image of the right side.

Figure 2:
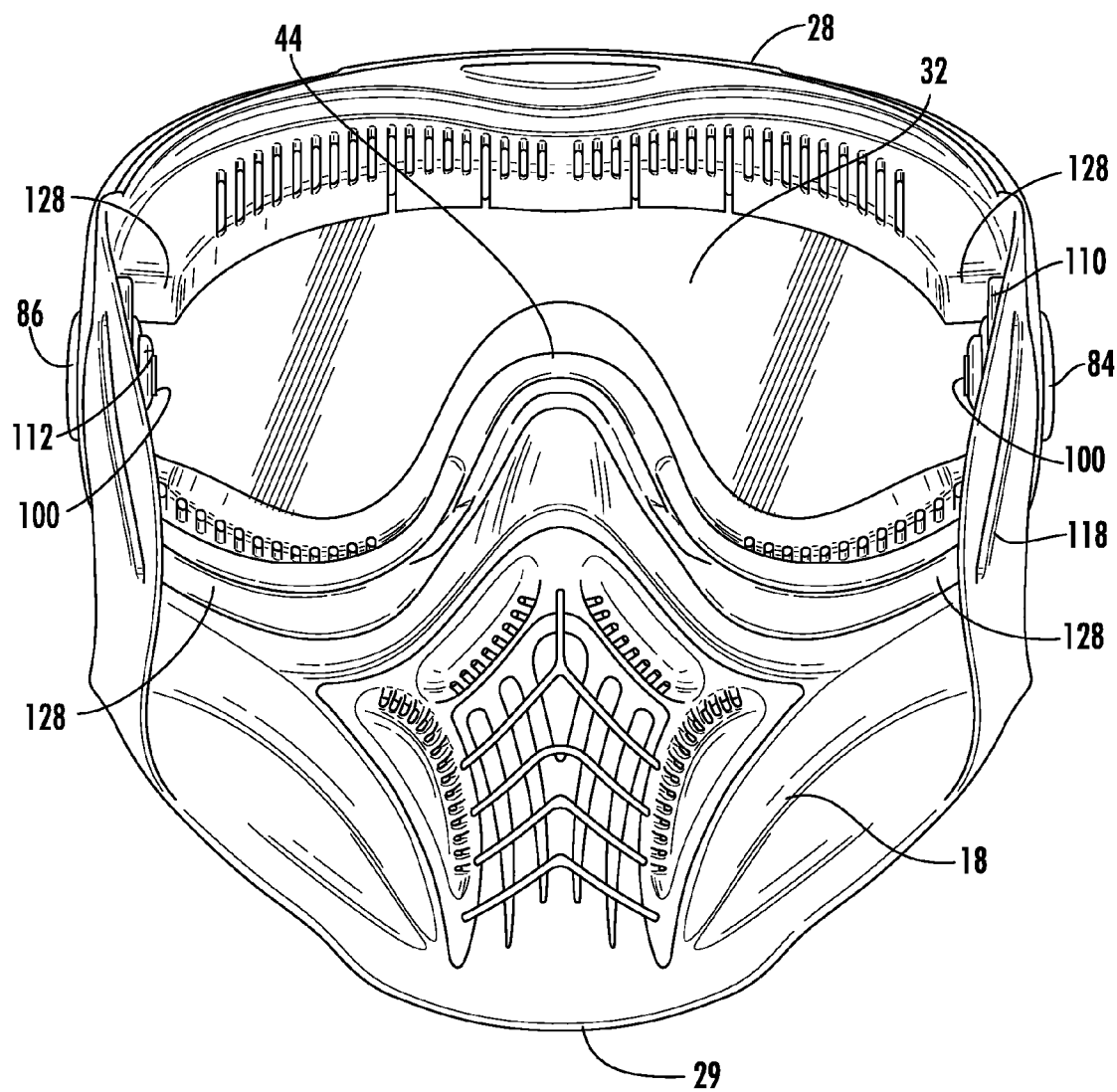
FIG. 2 shows a rear view of a face mask system according to the present invention, with the lens assembled on the mask body.

The retaining clips 110, 112 may include a sloped portion 122 opposite the strap slots 118, as shown in FIGS. 16-17. The sloped portion 122 may include a first stop portion 124 and a second stop portion 126. The inner side 18 of the mask body 12 is provided with a extension portions 128 positioned around the lens opening 32 as shown in FIGS. 18-19. The extension portions 128 may have foam or another impact resistant material attached thereto in order to provide a comfortable fit when worn by a user, and to provide additional shock resistance when a projectile impacts the mask 10 being worn by a user. The extension portions 128 are preferably positioned as shown in FIGS. 2, 18-19, to provide receiving spaces 130a, 130b adjacent the temple portions 24, 26 of the mask body 12. The receiving spaces 130a, 130b are sized to receive the sloped portion 122 of the retaining clips 110, 112.

When the retaining clips 110, 112 are rotated to lock the retaining elements 84, 86 in place, the sloped portions 122 of the retaining clips 110, 112 fit within the receiving spaces 130a, 130b, with the first stop portion 124 and the second stop portion 126 contacting the extension portions 128 at contact points 134a, 134b as shown in FIG. 19. The second stop portion 126 preferably includes a notch that engages contact point 134b of the extension portion 128. The notch 132 provides a locking portion for snapping engagement with the contact point 134b when the retaining clips 110, 112 are rotated into the locking position, as shown in FIG. 19. This provides an additional engagement means for maintaining the retaining clips 110, 112 in place when the mask 10 is fully assembled. When assembled, the receiving clips 110, 112 are positioned so that the strap slots 118 point rearward (relative to the user), and a strap (not pictured) may be attached. In addition, the mask body 12 may be provided with strap openings 119 at opposite ends of the mask body, as show in FIGS. 2, 18-19, that allow a strap to be threaded through the openings.

When the retaining clips 110, 112 are in a locked position, as in FIG. 19, the flanges 62, 64a, 64b are further secured within the grooves 36, 38a, 38b. The lens 48 will not slide or otherwise move in relation to the mask body 12. The nose portion 66 of the lens will not dislodge from the central receiving slot 46. This arrangement provides a secure face protection system, where the lens will not be dislodged even if hit from various angles with a projectile at high speed or other flying objects.

To disassemble the mask 10, right side retaining clip 110 is unlocked and rotated counterclockwise, while left side retaining clip 112 is rotated clockwise. The notches 134 of the retaining clips 110, 112 disengage the second contact point 134b. The sloped portions 122 allow the retaining clips 110, 112 to rotate in the directions as described. When the openings 114 are aligned so that the tabs 100 can pass through the openings 114, the retaining elements 84, 86 can be pushed out of the openings 76, 78, 80, 82. The lens 48 can now be removed by flexing the mask body 12, and disengaging the flanges 64a, 64b, from the grooves 36a, 36b, and removing the nose portion 66 of the lens 48 and nose extensions 68a, 68b from the central receiving slot 46.

The novel arrangement of the present invention provides increased protection in that the lens 48 is prevented from moving away from or otherwise dislodging from the mask body 12 when either are impacted by a projectile. Thus, in the sport of paintball, by way of example, if a projectile (paintball) is fired at a user and contacts the mask body 12 near an edge of the lens 48, the present face mask 10 will not allow the liquid paint from the projectile or the projectile shell to pass under or around the lens 48 into the interior of the mask body 12 or inner side 60 of the lens 48. Several known goggle systems suffer from problems when a paintball hits the mask near the nose area. The present invention provides a means for preventing separation of the lens and mask body upon impact. It should be appreciated that the lens 48 overlaps, or is sized larger than, the innermost edge of the lens supporting portion 34, as shown in FIGS. 1, 3 and 20. This overlap provides added protection to a user, as it is difficult for a projectile to force its way between the lens 48 and mask body 12.

In yet another embodiment of the present invention, as shown in FIGS. 21-24, additional means for securing the lens to the mask body are provided locking tabs 162a (left), 162b (right) are provided for locking the retaining clips 110, 112 in a secured position. The right locking tabs 162b, for example, includes a first lower wall 164, an angled vertical wall 166, a top clamp wall 168 having a contoured lowered surface 170, and an extension portion 172 extending from the top clamp wall 168. Left locking tab 162a is a mirror image of right locking tab 162b.

As shown in FIGS. 21-24, when the retaining clips 110, 112 is rotated to secure the retaining elements 84, 86, the locking tabs 162a, 162b are placed in a locking position with the first horizontal wall 162 inserted in the opening between the sloping wall 104a of the tabs 100, and the cam surface 116 of the openings 114 in the retaining clips 110, 112. The locking tabs 162a, 162b are snapped into place, with the contoured lowered surface 170 snapping partially in between the retaining clips 110, 112 and the inner surface 18 of the mask body 12. The extension portion 172 may be used to disengage the locking tabs 162a, 162b when a user seeks to remove the retaining clips 110, 112, retaining elements 84, 86, and/or the lens 48.

Figure 25:
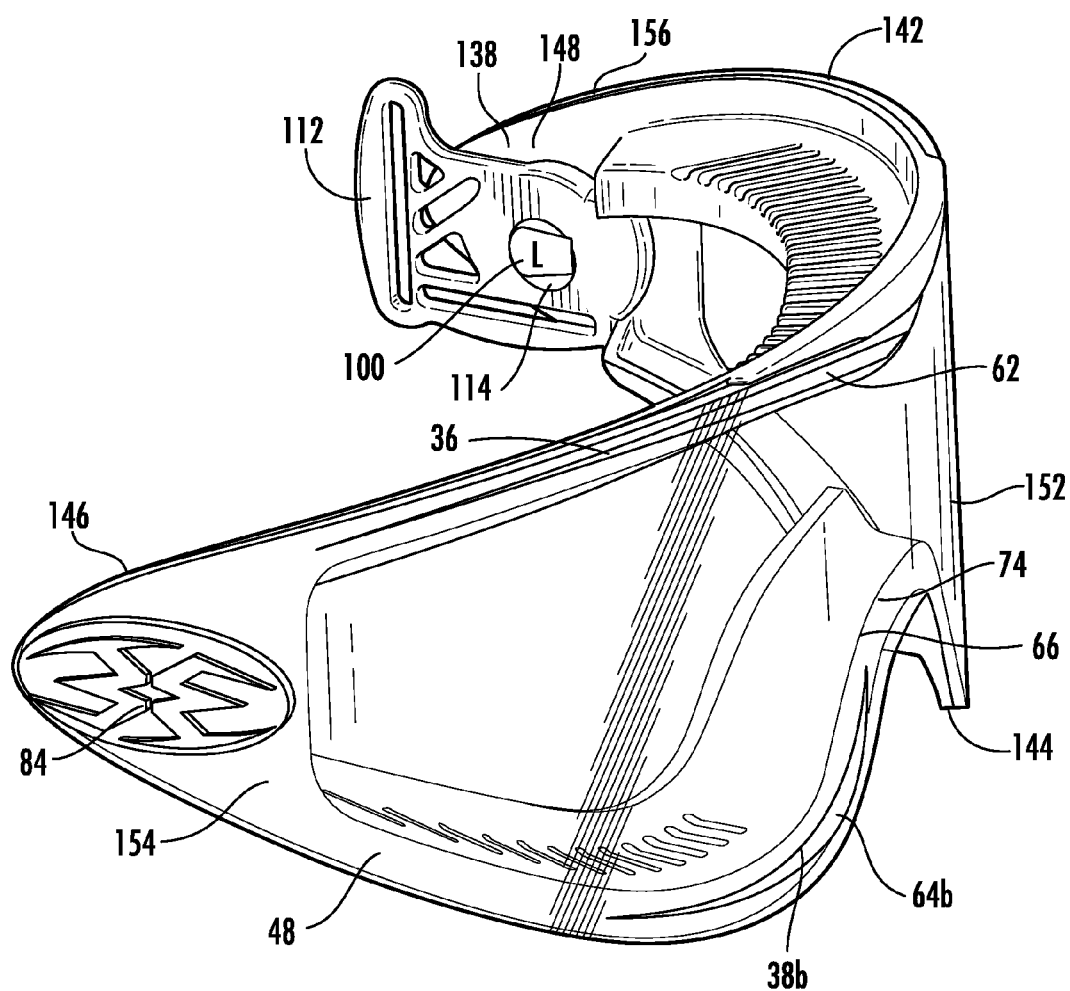
FIG. 25 shows a right front perspective view of a goggle system according to the present invention.
Figure 26:
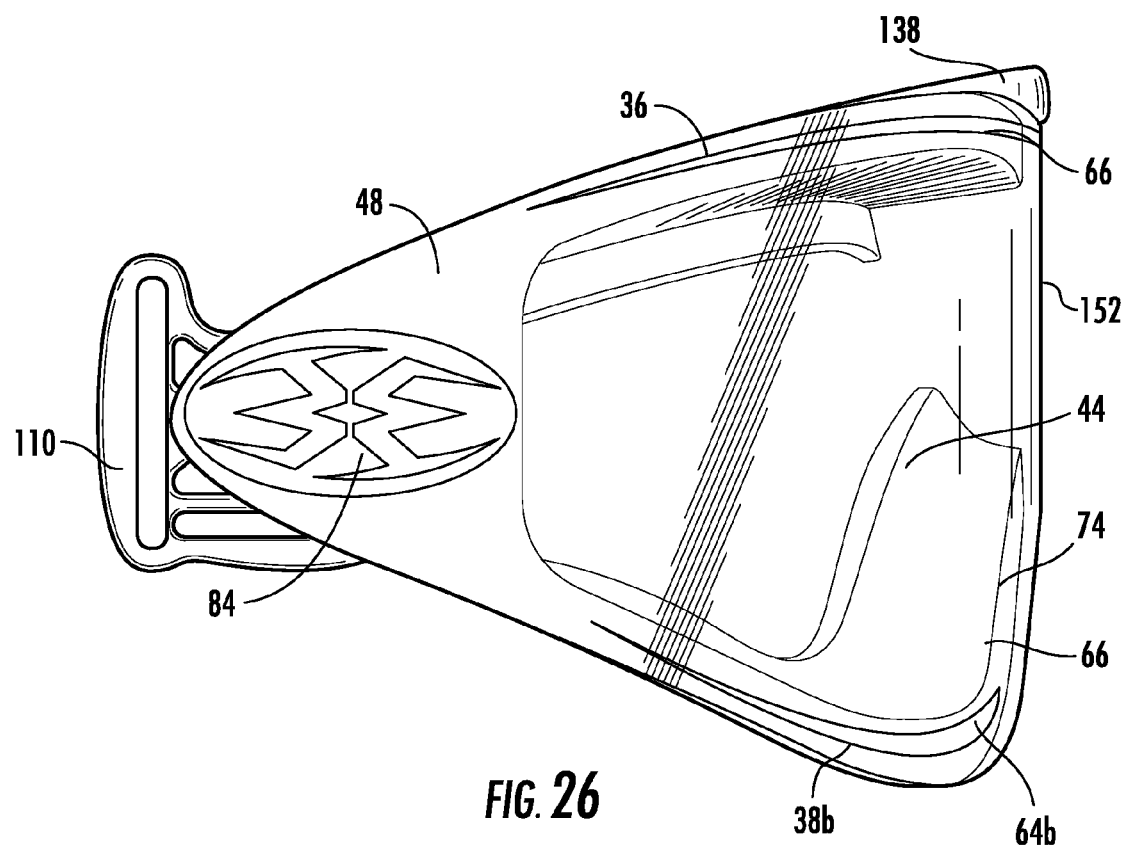
FIG. 26 shows a right side view of a goggle system according to the present invention.
Figure 27:
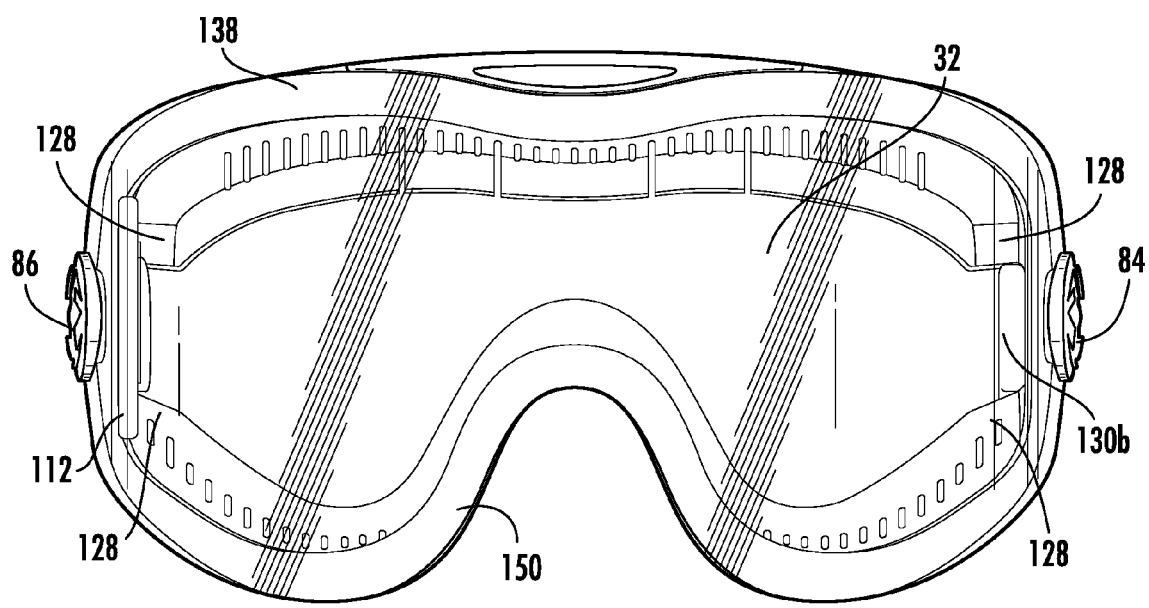
FIG. 27 shows a rear view of a goggle system according to the present invention.

The present invention also provides for a novel goggle system 200, having a similar lens and body arrangement as previously described, and as shown in FIGS. 25-27. Similarly to the mask body 12, a goggle frame 138 is provided having an upper portion 142, lower portion 144, right temple portion 146, left temple portion 148, inner side 150 facing a user, and an outer side 152 facing away from the user. The goggle frame 138 has a lens supporting portion 140 that is essentially the complete wall forming the outer side 152 of the goggle frame 138. The lens 48 substantially covers the entire outer side 152 of the goggle frame 138, so that the outer side 152 of the goggle frame 138 is effectively the same size as the lens 48. The goggle frame 138 has a right temple portion 154 with a right receiving opening (similar to the right temple portion 26 and the right receiving opening 76 of the mask body 12), and a left temple portion 156 with a left receiving opening (similar to the left temple portion 24 and left receiving opening 78 of the mask body 12).

The goggle frame includes an upper groove 62, and lower grooves 64a, 64b, as previously described above, for receiving the upper flange 62, and lower flanges 64a, 64b, of the lens 48. A central portion 44 is provided having a central support wall 74 that the nose portion 66 of the lens 48 rests against. In the goggle system 200 version of the present invention, it is not necessary to include a central receiving slot 46 or nose portion 22 of the goggle frame 138, as the lens completely covers the goggle frame 138, and therefore, it is unlikely that the lens 48 could be dislodged. However, a goggle system 200 according to the present invention may be formed with a central receiving slot 46 or nose portion 22, as described in detail above, and the lens may snap in place in the grooves, as discussed in detail above, providing yet another secure connection of the lens 48 to the goggle frame 138.

The inner side 150 of the goggle frame 138 includes extension portions 128, with receiving spaces 130a (left), 130b (right), as previously described. The retaining elements 84, 86 and retaining clips 110, 112 as previously described are used in connection with the goggle frame 138 to affix the lens 48 to the goggle frame 138.

Having thus described in detail several embodiments of the face mask and goggle systems of the present invention, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiment and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. A protective face mask system comprising:
    a flexible mask body comprising:
        a nose portion,
        right and left temple portions;
        right and left cheek portions;
        an opening formed in the mask configured to receive a lens, the opening having a right portion, a left portion, an upper portion and a lower portion;
        a lens supporting portion extending between the temple portions, the lens supporting portion positioned above the upper portion of the lens opening;
        a first groove formed in the lens supporting portion, the first groove extending along a majority of the length of the lens supporting portion;
        a second groove formed in the left cheek portion;
        a third groove formed in the right cheek portion;
        and, a lens having a front and a rear, the lens sized to be received upon and cover the lens opening, the lens including an upper portion, a lower portion, a right side, and a left side;
        an upper flange projecting from the rear of the upper portion of the lens, the upper flange extending along a majority of the length of the upper portion of the lens, the upper flange configured to be received within the first groove;
        a lower left flange projecting from the rear of the left side of the lens, the lower left flange configured to be received within the second groove;
        a lower right flange projecting from the rear of the right side of the lens, the lower right flange configured to be received within the third groove;
        wherein arranging the upper flange, lower left flange, and lower right flange within the first groove, second groove and third groove prevents movement of the lens relative to the mask body, and wherein the lens and mask body further comprise corresponding openings, which are in alignment when the lens is positioned on the mask body, and further comprising at least one fastener for securing the lens to the mask body, the fastener comprising a retaining element and a retaining clip, a portion of the retaining element insertable through the corresponding openings and the retaining clip, the retaining clip configured to secure the retaining element by rotating retaining clip relative to the retaining element.

2. The face mask system of claim 1, wherein the mask body further comprises a central portion positioned to the rear of and extending at least partially above the nose portion, and a central receiving slot positioned between the nose portion and the central portion, the central receiving slot configured to receive a central portion of the lens.

3. The face mask system of claim 1, wherein the mask body and lens include openings alignable when the lens is positioned on the mask body, and wherein the fastener further comprises:
    a retaining element including a retaining wall portion,
    a retaining extension extending from a face of the retaining wall portion and sized and shaped to insert into the mask body opening and the corresponding lens opening; and,
    a retaining clip rotatable from a first unlocked position to a second lock position, the retaining clip including a retaining clip opening sized and shaped to receive at least a portion of the shaped retaining extension.

4. The face mask system of claim 3, wherein the retaining extension of the retaining element is inserted from an outside surface of the lens through the opening in the lens and through the corresponding opening in the mask body, and the retaining clip engages the retaining extension adjacent an inner surface of the mask body.

5. A face mask system comprising:
    a flexible mask body comprising:
        a nose portion,
        right and left temple portions;
        left and right cheek portions;
        an opening formed in the mask configured to receive a lens, the opening having a right portion, a left portion, an upper portion and a lower portion;
        a lens supporting portion extending between the temple portions, the lens supporting portion positioned above the upper portion of the lens opening;
        a first groove formed in the lens supporting portion, the first groove extending along the majority of the length of the lens supporting portion;
        a second groove formed in the left cheek portion;
        a third groove formed in the right cheek portion;
    and, a lens having a front and a rear, the lens sized to be received upon and cover the lens opening, the lens including an upper portion, a lower portion, a right side, and a left side;
    an upper flange projecting from the rear of the upper portion of the lens, the upper flange extending along a majority of the length of the upper portion of the lens, the upper flange configured to be received within the first groove;
    a lower left flange projecting from the rear of the left side of the lens, the lower left flange configured to be received within the second groove;
    a lower right flange projecting from the rear of the right side of the lens, the lower right flange configured to be received within the third groove;
    wherein arranging the upper flange, lower left flange, and lower right flange within the first groove, second groove and third groove prevents movement of the lens relative to the mask body;
    a lens having a right temple portion including an opening for alignment with the right temple portion of the mask body when the lens is in an assembled position, and a left temple portion including an opening for alignment with the left temple portion of the mask body when the lens is in an assembled position;

at least one two-piece fastener for securing the lens to the mask body when the openings are aligned, the fastener comprising: a retaining element including a retaining wall portion, a retaining extension extending from a face of the retaining wall portion sized and shaped to insert into one of the mask body openings and a corresponding lens opening when the lens is in an assembled positioned;

and, a retaining clip including a retaining clip opening sized and shaped to receive at least a portion of the retaining extension, the retaining clip moveable from a first unlocked position to a second locked position.

6. The face mask system of claim 5, wherein the retaining extension of the retaining element is inserted from an outside surface of the lens through the opening in the lens and through the corresponding opening in the mask body, and the retaining clip engages the retaining extension adjacent an inner surface of the mask body.

7. The face mask system of claim 5, wherein the fastener secures the lens to the mask body when the retaining extension is inserted through an opening in the retaining clip, and the retaining clip is turned relative to the retaining element at least about a quarter turn from a first position to a second position.

* * * * *